US012569470B2

(12) United States Patent
Lee

(10) Patent No.: US 12,569,470 B2
(45) Date of Patent: Mar. 10, 2026

(54) VASODILATOR AND USE THEREOF

(71) Applicant: Bioradical Research Institute Corp., Yokohama (JP)

(72) Inventor: Masaichi Lee, Yokohama (JP)

(73) Assignee: Bioradical Research Institute Corp., Yokohama (JP)

( * ) Notice: Subject to any disclaimer, the term of this patent is extended or adjusted under 35 U.S.C. 154(b) by 753 days.

(21) Appl. No.: 17/783,104

(22) PCT Filed: Dec. 18, 2020

(86) PCT No.: PCT/JP2020/047525
§ 371 (c)(1),
(2) Date: Jun. 7, 2022

(87) PCT Pub. No.: WO2021/125345
PCT Pub. Date: Jun. 24, 2021

(65) Prior Publication Data

US 2023/0330066 A1 Oct. 19, 2023

(30) Foreign Application Priority Data

Dec. 18, 2019 (JP) ................................ 2019-228695

(51) Int. Cl.
*A61K 31/4155* (2006.01)
*A61P 9/08* (2006.01)

(52) U.S. Cl.
CPC ............ *A61K 31/4155* (2013.01); *A61P 9/08* (2018.01)

(58) Field of Classification Search
CPC .............................. A61K 31/4155; A61P 9/08
See application file for complete search history.

(56) References Cited

U.S. PATENT DOCUMENTS

| | | | |
|---|---|---|---|
| 5,314,998 A | 5/1994 | Smith et al. | |
| 6,312,478 B1 | 11/2001 | Goettel et al. | |
| 6,399,767 B1 | 6/2002 | Horne et al. | |
| 7,060,822 B1 * | 6/2006 | Arnold ................ | C07D 401/06 544/371 |
| 2007/0123577 A1 | 5/2007 | Miyata et al. | |
| 2010/0016396 A1 | 1/2010 | Moto | |
| 2012/0035187 A1 | 2/2012 | Ohta et al. | |
| 2016/0122341 A1 | 5/2016 | Vakalopoulos et al. | |
| 2017/0291889 A1 | 10/2017 | Barden et al. | |
| 2017/0313700 A1 | 11/2017 | Vakalopoulos et al. | |
| 2018/0147875 A1 | 5/2018 | Santo et al. | |
| 2022/0110916 A1 | 4/2022 | Makino et al. | |

FOREIGN PATENT DOCUMENTS

| | | |
|---|---|---|
| CA | 2103972 A1 | 3/1994 |
| JP | S63-2045 A | 1/1988 |
| JP | H04-131842 A | 5/1992 |
| JP | H05-45787 A | 2/1993 |
| JP | H06-179828 A | 6/1994 |
| JP | H10-305665 A | 11/1998 |
| JP | 2000-514463 A | 10/2000 |
| JP | 2001-524987 A | 12/2001 |
| JP | 2006-008618 A | 1/2006 |
| JP | 2016-522214 A | 7/2016 |
| JP | 2017-528494 A | 9/2017 |
| JP | 2017-537922 A | 12/2017 |
| JP | 2018-089960 A | 6/2018 |
| WO | 2005/054205 A1 | 6/2005 |
| WO | 2008/093639 A1 | 8/2008 |
| WO | 2010/087306 A1 | 8/2010 |
| WO | 2010/087313 A1 | 8/2010 |
| WO | 2010/087315 A1 | 8/2010 |
| WO | 2020/158225 A1 | 8/2020 |

OTHER PUBLICATIONS

Decision of Refusal issued in corresponding Japanese Patent Application No. 2020-569437 dated Jan. 10, 2023.
Sommani et al., "Effects of Edaravone on Singlet Oxygen Released from Activated Human Neutrophils," Journal of Pharmacological Society, 103: 117-120 (2007).
Knox et al., "Discovery and Clinical Evaluation of MK-8150, A Novel Nitric Oxide Donor With a Unique Mechanism of Nitric Oxide Release," Journal of the American Heart Association, e003493 (2016).
Lesnov et al., "Di-(1-hexyl-5-hydroxy-3-methyl-4-pyrazolyl)methane as an Extraction Reagent for Metal Ions," (see English abstract and ISR).
Pavolov et al., "Biological activity of some pyrazolone derivatives," Pharmaceutical Chemistry Journal, 32: 370-372 (1998) (see ISR).
International Search Report issued in corresponding International Patent Application No. PCT/JP2019/049670 dated Feb. 4, 2020.
Khairnar et al., "Organophosphane-Catalyzed Direct Beta-Acylation of 4-Arylidene Pyrazolones and 5-Arylidene Thiazolones with Acyl Chlorides," Organic Letters, 22: 6868-6872 (2020).
(Continued)

*Primary Examiner* — Kevin E Weddington
(74) *Attorney, Agent, or Firm* — Morgan, Lewis & Bockius LLP

(57) ABSTRACT

The present invention provides a vasodilator capable of dilating a blood vessel even in the presence of ROS. A vasodilator of the present invention includes:

a compound represented by the following formula (1) or a salt thereof:

(1)

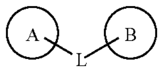

where in the formula (1), an A ring and a B ring may be the same or different and are each a pyrazole ring having a substituent or a pyrazoline ring having a substituent, and L is a saturated or unsaturated hydrocarbon group.

17 Claims, 13 Drawing Sheets

(56) References Cited

OTHER PUBLICATIONS

Khairnar et al., “Diversity-Oriented Synthesis of Spiropentadiene Pyrazolones and 1H-Xoepino[2,3-c]pyrazoles from Doubly Conjugated Pyrazolones via Intramolecular Wittig Reaction,” Organic Letters, 22 (12): 4760-4765 (2020).
Dirat et al., “Regioselective synthesis of 4-(2-alkyl-5-methyl-2H-pyrazol-3-yl)-piperidines,” Tetrahedron Letters, 47: 1729-1731 (2006).
International Search Report issued in corresponding International Patent Application No. PCT/JP2020/047525 dated Mar. 2, 2021.
Office Action issued in the related U.S. Appl. No. 17/424,334, dated Sep. 27, 2024.
Hall A. et al., “Novel Methylene-Linked Heterocyclic EP1 Receptor Antagonists”, Bioorganic & Medicinal Chemistry Letters, Mar. 2008, 18(5): 1592-1597.
Yang X. et al., “Synthesis and Antioxident Activities of Novel4,4'-arylmethylene-bis (1h-pyrazole-5-ol)s from Lignin”, Chinese Journal of Chemistry, Mar. 2012, 30(3): 670-674.
Office Action issued in the corresponding JP Patent Application No. 2024-073944, issued Aug. 5, 2025.
Parker, S. J., & Watkins, P. E. (2001). Experimental models of gram-negative sepsis. British journal of surgery, 88(1), 22-30, https://doi.org/10.1046/j.1365-2168.2001.01632.x.
Gorabi, A. M., Kiaie, N., Khosrojerdi, A., Jamialahmadi, T., Al-Rasadi, K., Johnston, T. P., & Sahebkar, A. (2022). Implications for the role of lipopolysaccharide in the development of atherosclerosis. Trends in cardiovascular medicine, 32(8), 525-533, https://doi.org/10.1016/j.tcm.2021.08.015.—abstract.
Ahmed, S. H., He, Y. Y., Nassief, A., Xu, J., Xu, X. M., & Hsu, C. Y. (2000). Effects of lipopolysaccharide priming on acute ischemic brain injury. Stroke, 31(1), 193-199, https://doi.org/10.1161/01.STR.31.1.193.
Chen, H., Bai, C., & Wang, X. (2010). The value of the lipopolysaccharide-induced acute lung injury model in respiratory medicine. Expert review of respiratory medicine, 4(6), 773-783, https://doi.org/10.1586/ers.10.71—abstract.
Nazem, A., Sankowski, R., Bacher, M., & Al-Abed, Y. (2015). Rodent models of neuroinflammation for Alzheimer’s disease. Journal of neuroinflammation, 12(1), 74, https://doi.org/10.1186/s12974-015-0291-y.
Doi, K., Leelahavanichkul, A., Yuen, P. S., & Star, R. A. (2009). Animal models of sepsis and sepsis-induced kidney injury. The Journal of clinical investigation, 119(10), 2868-2878, https://doi.org/10.1172/JCI39421.
Southey, A., Tanaka, S., Murakami, T., Miyoshi, H., Ishizuka, T., Sugiura, M., . . . & Sugita, T. (1998). Pathophysiological role of nitric oxide in rat experimental colitis. International journal of immunopharmacology, 19 (11-12), 669-676, https://doi.org/10.1016/S0192-0561(97)00107-0.
Dumitrescu, A. L., Abd El-Aleem, S., Morales-Aza, B., & Donaldson, L. F. (2004). A model of periodontitis in the rat: effect of lipopolysaccharide on bone resorption, osteoclast activity, and local peptidergic innervation. Journal of Clinical Periodontology, 31(8), 596-603, https://doi.org/10.1111/j.1600-051X.2004.00528.x.
Finar and Godfrey, “The Preparation and Properties of Some Derivative of 1-Phenylpyrazole”, Journal of the Chemical Society, pp. 2293-2298 (1954).
Patani and LaVoie, “ Bioisosterism: A Rational Approach in Drug Design”, Chemical Reviews, vol. 96, No. 8, pp. 3147-3176 (1996).
Attaryan et al., Extrusion of Formaldehyde from Bis(pyrazolylmethyl) Ether on Heating, Russian Journal of General Chemistry, vol. 77, No. 6, pp. 1139-1140 (2007).
Ai-xiang Tian, “The key role of -CH3 steric hindrance in bis-(pyrazolyl) ligand on polyoxometalate-based compounds”, Dalton Transactions, vol. 43, pp. 8405-8413 (2014).
Notice of Payment of Restoration Fee for Unity issued in Chinese Patent Application No. 202180059651.6, dated Mar. 8, 2025.
Ismail et al., “Carotid Artery Stenosis: A Look Into the Diagnostic and Management Strategies, and Related Complications”, Cureus, vol. 15 No. 5, 2023, pp. 1-16.
Premer et al., “Rethinking Endothelial Dysfunction as a Crucial Target in Fighting Heart Failure”, Mayo Clin Proc Inn Qual Out, vol. 3, No. 1, 2019, pp. 1-13.
Rajendran et al., “The Vascular Endothelium and Human Diseases”, International Journal of Biological Sciences, vol. 9, No. 10, 2013, pp. 1057-1069.
Silva et al., “The ”Silent Enemy“ Called Renal Artery Stenosis: A Mini-Review”, Journal of Vascular Diseases, vol. 4, No. 10, 2025, pp. 1-26.
Sun et al., “Role of Endothelial Dysfunction in Cardiovascular Diseases: The Link Between Inflammation and Hydrogen Sulfide”, Frontiers in Pharmacology, vol. 10, Article 1568, Jan. 2020, pp. 1-15.
Wijeratne et al., “Carotid artery stenosis and inflammatory biomarkers: the role of inflammation-induced immunological responses affecting the vascular systems”, Annals of Translational Medicine, vol. 8, No. 19, 2020, pp. 1-9.
Office Action issued in Japanese Patent Application No. 2022-539533, dated Nov. 11, 2025.

* cited by examiner 0 min 30 min 60 min 90 min 120 min 150 min 180 min 0 min 30 min 60 min 90 min 20 min 50 min 180 min

VASODILATOR AND USE THEREOF

TECHNICAL FIELD

The present invention relates to a vasodilator and use thereof.

BACKGROUND ART

For diseases such as angina pectoris, caused by vascular stenosis, vasodilators such as nitroglycerin, nitric acid preparations, and the like, which provide nitric oxide (NO), are used. These vasodilators supply NO so that the action of increased NO in the blood dilates blood vessels (Non-Patent Literature 1).

Citation List

Non-Patent Literature

Non-Patent Literature 1: Knox, Clayton D. et al., "Discovery and Clinical Evaluation of MK-8150, A Novel Nitric Oxide Donor with a Unique Mechanism of Nitric Oxide Release," Journal of American Heart Association, 2016, vol. 5, no. 9, e003493.

SUMMARY OF INVENTION

Technical Problem

The vasodilator is effective in the absence of reactive oxygen species (ROS). However, the inventors of the present invention have found that, in the presence of ROS, NO reacts with ROS to form highly oxidative peroxynitrite (ONOO$^{31}$) and does not contribute to vasodilation. Peroxynitrite is highly cytotoxic and may cause vascular disorder, resulting in various diseases such as hemorrhage.

With the foregoing in mind, it is an object of the present invention to provide a vasodilator capable of dilating a blood vessel even in the presence of ROS.

Solution to Problem

In order to achieve the above object, the present invention provides a vasodilator including:

a compound represented by the following formula (1) or a salt thereof:

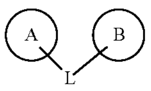

(1)

where in the formula (1), an A ring and a B ring may be the same or different and are each a pyrazole ring having a substituent or a pyrazoline ring having a substituent, and L is a saturated or unsaturated hydrocarbon group.

The present invention also provides a bloodstream-improving agent (hereinafter also referred to as an improving agent), including the vasodilator according to the present invention.

The present invention also provides a vascular disorder protective agent (hereinafter also referred to as a protective agent), including the vasodilator according to the present invention.

The present invention also provides a pharmaceutical for a disease caused by vascular stenosis (hereinafter also referred to as a pharmaceutical), including the vasodilator according to the present invention.

The present invention also provides a vasodilation method using the vasodilator according to the present invention.

Advantageous Effects of Invention

According to the present invention, by including the compound represented by the formula (1) or a salt thereof, blood vessels can be dilated even in the presence of ROS.

BRIEF DESCRIPTION OF DRAWINGS

In FIG. 10, (A) shows the result of a thin blood vessel, (B) shows the result of a medium blood vessel, and (C) shows the result of a thick blood vessel.

DESCRIPTION OF EMBODIMENTS

<Vasodilator>

Figure 1A:
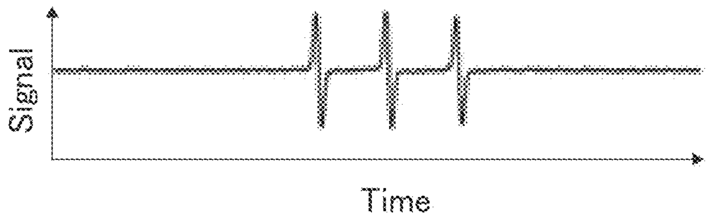
FIG. 1 shows graphs showing ESR results in Example 3.

As described above, the vasodilator of the present invention includes:

a compound represented by the following formula (1) or a salt thereof:

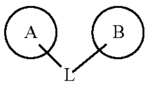

(1)

where in the formula (1), an A ring and a B ring may be the same or different and are each a pyrazole ring having a substituent or a pyrazoline ring having a substituent, and L is a saturated or unsaturated hydrocarbon group.

The vasodilator of the present invention is characterized in that it includes a compound represented by the formula (1) or a salt thereof, and other configurations and conditions are not particularly limited. It is presumed that the vasodilator of the present invention scavenges reactive oxygen species (ROS) by the following mechanism to reduce oxidative stress and induce vasodilation. Note that the present invention is not limited in any way to the following presumption. In a compound represented by the formula (1) or a salt thereof, it is presumed that a pyrazole ring or a pyrazoline ring linked by a functional group L alone or together with a functional group L forms a conjugated system. It is also presumed that, since the stability of the compound is high due to the conjugated system formed, the compound of the formula (1) can absorb the radical or energy possessed by the ROS and functions as a scavenger of ROS. It is presumed that, as a result, oxidative stress is alleviated, and vasodilation is induced through the improvement of NO production by vascular endothelial cells. Further, it is presumed that since the vasodilator of the present invention can scavenge ROS, the generation of peroxynitrite from NO produced by vascular endothelial cells is suppressed. Therefore, it is presumed that the vasodilator of the present invention induces vasodilation because NO produced by vascular endothelial cells is not converted to peroxynitrite and acts as NO on vascular endothelial cells. It is also presumed that the vasodilator of the present invention can protect (suppress) vascular disorder because NO produced by vascular endothelial cells is not converted to peroxynitrite or such a conversion is suppressed.

As to the expression “vasodilation” in the present invention, for example, it is acceptable as long as blood vessels are (significantly) dilated as compared to the case of absence (non-administration condition) of the vasodilator of the present invention, and the blood vessel may contract as compared to the initiation (administration initiation). In this case, the “vasodilation” may also be referred to as “suppression of vasoconstriction,” “reduction of vasoconstriction,” or the like, for example. The dilation of the blood vessel can be evaluated, for example, based on the diameter of the blood vessel to be evaluated (diameter hereinafter also referred to as “blood vessel diameter”). The blood vessel to be examined is, for example, a blood vessel having a diameter of 50 μm or less.

The blood vessel diameter means, for example, a blood vessel inner diameter. The measuring time of the blood vessel diameter is, for example, the late vasoconstriction (corresponding to the late diastole of the heart). In the measurement of the blood vessel diameter, the longest diameter of an area in which blood (red blood cells) is present when a blood vessel to be measured is optically observed may be measured as the blood vessel diameter, for example.

The vasodilator of the present invention can scavenge ROS as described above. Thus, the vasodilator of the present invention can also be referred to as an antioxidant, for example. The “antioxidant” means, for example, an agent that scavenges ROS. Examples of the ROS include radical species such as hydroxyl radical (·OH), alkoxy radical (LO·), peroxy radical (LOO·), hydroperoxy radical (HOO·), nitrogen monoxide (NO·), nitrogen dioxide ($NO_2$·), superoxide anion ($O_2^-$), and the like; and non-radical species such as singlet oxygen ($^1O_2$), ozone ($O_3$), hydrogen peroxide ($H_2O_2$), and the like. The vasodilator of the present invention may scavenge, for example, any one of or two or more of the ROS, and it is preferable to scavenge singlet oxygen ($^1O_2$). The scavenging of the ROS can also be referred to as, for example, elimination of ROS. The scavenging of the ROS is carried out, for example, by the vasodilator of the present invention donating a hydrogen atom to the ROS and converting the ROS into other molecules (e.g., water) that are more stable. The vasodilator of the present invention may also be referred to as, for example, a scavenger of ROS, radical species, or singlet oxygen, or an eliminator of ROS, radical species, or singlet oxygen. In addition, the vasodilator of the present invention can suppress or prevent oxidation by ROS of other molecules coexisting, for example. Thus, the vasodilator of the present invention can also be referred to as an oxidation inhibitor or an oxidation depressant, for example.

The ROS scavenging ability can be evaluated, for example, by a reactive oxygen evaluation method using 2, 2, 6, 6-tetramethyl-4-piperidone (TMPD). When the ROS is singlet oxygen, the singlet oxygen-scavenging ability can be measured according to Example 3 described below.

Each substituent in the compound represented by the formula (1) will be described below with reference to examples. Regarding the description of each substituent, reference can be made to specific examples in the description of other substituents, unless otherwise stated. In addition, when there is no particular reference in the following description, the description of the compound represented by the formula (1) can be applied to the description of the salt of the compound represented by the formula (1), for example.

When the compound represented by the formula (1) has an asymmetric carbon atom, the compound represented by the formula (1) may be present as, for example, a racemate, an enantiomer of R and S thereof, or a mixture of R and S in any proportion. The compound represented by the formula (1) may have two or more asymmetric centers. In this case, the compound represented by the formula (1) may contain a diastereomer and a mixture thereof. When the compound represented by the formula (1) has a double bond in a molecule, the compound of the present invention may include, for example, a form of a geometric isomer of cis and trans isomers.

In the formula (1), the A ring and the B ring may be the same or different and are each a pyrazole ring having a substituent or a pyrazoline ring having a substituent. The pyrazole ring having a substituent may be, for example, a pyrazole ring represented by the following formula (2). Further, the pyrazoline ring having a substituent may be, for example, a pyrazoline ring represented by the following formula (3).

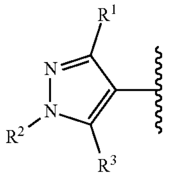

(2)

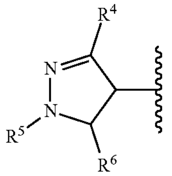

(3)

In the formula (2), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably a hydrogen atom, a halogen atom, or an alkyl group.

Examples of the halogen atom include a fluorine atom, a chlorine atom, a bromine atom, and an iodine atom.

Examples of the alkyl group include linear, branched, or cyclic saturated or unsaturated alkyl groups having 1 to 20 or 1 to 10 carbon atoms. Specific examples of the alkyl group include a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group, a t-hexyl group, an n-heptyl group, an i-heptyl group, a t-heptyl group, an n-octyl group, an i-octyl group, a t-octyl group, an n-nonyl group, an i-nonyl group, a t-nonyl group, an n-decyl group, an i-decyl group, a t-decyl group, an n-undecyl group, an i-undecyl group, an n-dodecyl group, an i-dodecyl group, an n-tridecyl group, an i-tridecyl group, an n-tetradecyl group, an i-tetradecyl group, an n-pentadecyl group, an i-pentadecyl group, an n-hexadecyl group, an i-hexadecyl group, an n-heptadecyl group, an i-heptadecyl group, an n-octadecyl group, an i-octadecyl group, an n-nonadecyl group, and an i-nonadecyl group. The alkyl group is preferably, for example, a linear saturated alkyl group having 1 to 6 carbon atoms, and more preferably a methyl group or an ethyl group.

In the alkoxy group (RO−), R is an alkyl group, and reference can be made to the description of the alkyl group described above.

In the hydroxyalkyl group (HOR−), R is an alkyl group, and reference can be made to the description of the alkyl group described above.

In the acyl group (RCO−), R is an alkyl group, and reference can be made to the description of the alkyl group described above.

Examples of the alkenyl group include those having one or more double bonds in the alkyl group. Examples of the alkenyl group include alkenyl groups having 2 to 20 carbon atoms, preferably 2 to 6 carbon atoms, and specific examples thereof include a vinyl group, an allyl group, a 1-propenyl group, a 2-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, and a 2-methyl-2-butenyl group.

Examples of the alkynyl group include those having one or more triple bonds in the alkyl group. Examples of the alkynyl group include alkynyl groups having 2 to 20 carbon atoms, preferably 2 to 6 carbon atoms, and specific examples thereof include an ethynyl group, a 1-propynyl group, a 2-propynyl group, a 1-butynyl group, a 2-butynyl group, a 3-butynyl group, a 1-methyl-2-propynyl group, a 1-pentinyl group, a 2-pentinyl group, a 3-pentinyl group, a 4- pentinyl group, and a 1-methyl-3-butynyl group. The alkynyl group may further have, for example, one or more double bonds.

The aryl group that may have a substituent may be an aryl group, or the aryl group may be substituted with a substituent. The aryl group that may have a substituent is, for example, an aryl group having 6 to 20 total carbon atoms, including the number of carbon atoms in the substituent, and specific examples thereof include a phenyl group, a tolyl group, a xylyl group, an alkyloxyphenyl group (e.g., a methoxyphenyl group, an ethoxyphenyl group), a hydroxyphenyl group, a halogenophenyl group (e.g., a fluorophenyl group, a chlorophenyl group, a bromophenyl group), an alkylphenyl group (e.g., a methylphenyl group, an ethylphenyl group, a propylphenyl group), a cyanophenyl group, a propyloxyphenyl group, and a 4-sulfophenyl group, and a phenyl group or a 4-sulfophenyl group is preferable.

In the formula (2), $R^2$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and is preferably an alkyl group or an aryl group that may have a substituent. The alkyl group is preferably a linear saturated alkyl group having 1 to 6 carbon atoms, and more preferably a methyl group or an ethyl group. As the aryl group that may have a substituent, a phenyl group or a 4-sulfophenyl group is preferable.

In the formula (2), $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and is preferably a hydrogen atom, a halogen atom, or a hydroxy group. The alkyl group is preferably a linear saturated alkyl group having 1 to 6 carbon atoms, and more preferably a methyl group or an ethyl group.

In the formula (3), $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably a hydrogen atom, a halogen atom, or an alkyl group. The alkyl group is preferably a linear saturated alkyl group having 1 to 6 carbon atoms, and more preferably a methyl group or an ethyl group.

In the formula (3), $R^5$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably an alkyl group or an aryl group that may have a substituent. The alkyl group is preferably a linear saturated alkyl group having 1 to 6 carbon atoms, and more preferably a methyl group or an ethyl group. As the aryl group that may have a substituent, a phenyl group or a 4-sulfophenyl group is preferable.

In the formula (3), $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and is preferably a hydrogen atom, an oxygen atom, a halogen atom, or a hydroxy group.

In the formula (1), L is a saturated or unsaturated hydrocarbon group. Examples of L include saturated hydrocarbon groups such as an alkyl group and the like and unsaturated hydrocarbon groups such as an alkenyl group, an alkynyl group, and the like. Regarding the alkyl group, reference can be made to the description as to the alkyl group in $R^1$. The number of carbon atoms of the main chain in L is preferably an odd number, and, as a specific example, the number of carbon atoms is preferably 1, 3, 5, or 7, more preferably 1, 3 or 5, and still more preferably 3.

Examples of the alkenyl group include those having one or more double bonds in the alkyl group. Examples of the alkenyl group include alkenyl groups having 2 to 20 carbon atoms, preferably 2 to 6 carbon atoms, and specific examples thereof include a vinyl group, an allyl group, a 1-propenyl group, a 2-propenyl group, an isopropenyl group, a 1-butenyl group, a 2-butenyl group, a 3-butenyl group, a 2-methylallyl group, a 1-pentenyl group, a 2-pentenyl group, a 3-pentenyl group, a 4-pentenyl group, and a 2-methyl-2-butenyl group.

Examples of the alkynyl group include those having one or more triple bonds in the alkyl group. Examples of the alkynyl group include alkynyl groups having 2 to 20 carbon atoms, preferably 2 to 6 carbon atoms, and specific examples thereof include an ethynyl group, a 1-propynyl group, a 2-propynyl group, a 1-butynyl group, a 2-butynyl group, a 3-butynyl group, a 1-methyl-2-propynyl group, 1-pentinyl group, 2-pentinyl group, 3-pentinyl group, 4-pentinyl group, and 1-methyl-3-butynyl group. The alkynyl group may further have, for example, one or more double bonds.

L is preferably an unsaturated hydrocarbon group having 1 to 6 carbon atoms, more preferably an alkenyl group having 2 to 6 carbon atoms, and specific examples thereof include a 1-propenyl group and a 2-propenyl group.

The compound represented by the formula (1) preferably includes a compound represented by the following formula (4):

(4)

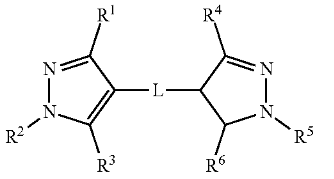

In the formula (4), $R^1$ is a hydrogen atom, a halogen atom, or an alkyl group,
$R^2$ is an alkyl group or an aryl group that may have a substituent,
$R^3$ is a hydrogen atom, a halogen atom, or a hydroxy group,
$R^4$ is a hydrogen atom, a halogen atom, or an alkyl group,
$R^5$ is an alkyl group or an aryl group that may have a substituent,
$R^6$ is a hydrogen atom, an oxygen atom, a halogen atom, or a hydroxy group, and
L is a saturated or unsaturated hydrocarbon group having 1 to 6 carbon atoms.

In the formula (4), $R^1$ is a hydrogen atom or an alkyl group,
$R^2$ is an alkyl group or an aryl group that may have a substituent,
$R^3$ is a hydroxy group,
$R^4$ is a hydrogen atom or an alkyl group,
$R^5$ is an alkyl group or an aryl group that may have a substituent,
$R^6$ is an oxygen atom or a hydroxy group, and
L is preferably an unsaturated hydrocarbon group having 1 to 6 carbon atoms, and more preferably an unsaturated hydrocarbon group having 1, 3, or 5 carbon atoms.

As a specific example, the compound represented by the formula (1) preferably includes a compound represented by the following formula (5) because, for example, it can suppress the decomposition reaction in an aqueous solution or an aqueous solvent such as a phosphate buffer, it can scavenge the superoxide and the singlet oxygen, it has no or low cytotoxicity, and it can suppress the generation of a byproduct having cytotoxicity even after the reaction with singlet oxygen. The compound of the following formula (5) can dilate blood vessels more effectively, for example. The compound of the following formula (5) may also be referred to as, for example, 2,4-dihydro-4-[3-(1-ethyl-5-hydroxy-3-methyl-1H-pyrazol-4-yl)-2-propen-1-ylidene]-2-ethyl-5-methyl-3H-pyrazol-3-one. Hereinafter, the compound of the following formula (5) is also referred to as BisEp-C3.

(5)

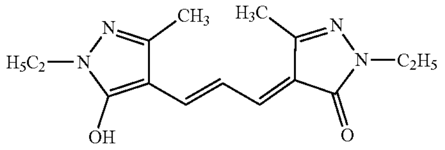

The compound represented by the formula (1) preferably includes a compound represented by the following formula (6) because, for example, it can suppress the decomposition reaction in an aqueous solution or an aqueous solvent such as a phosphate buffer, it can scavenge the superoxide and the singlet oxygen, and it has no or low cytotoxicity. The compound of the following formula (6) may also be referred to as, for example, 2,4-dihydro-4-[3-(5-hydroxy-3-methyl-1-phenyl-1H-pyrazol-4-yl)-2-propen-1-ylidene]-5-methyl-2-phenyl-3H-pyrazol-3-one. The compound of the following formula (6) is, for example, a compound registered under the CAS Registration No. 27981-68-6. Hereinafter, the compound of the following formula (6) is also referred to as ED2AP.

(6)

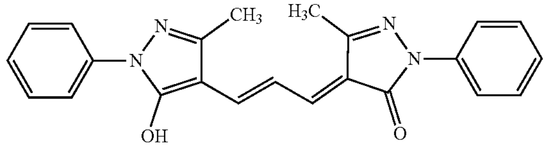

The compound represented by the formula (1) includes, for example, a compound represented by the following formula (7). The compound of the following formula (7) may also be referred to as, for example, 4-[4,5-dihydro-4-[3-[5-hydroxy-3-methyl-1-(4-sulfophenyl)-1H-pyrazol-4-yl]-2-propen-1-ylidene]-3-methyl-5-oxo-1H-pyrazol-1-yl]-benzenesulfonic acid. In the compound represented by the following formula (7), hydrogen in the sulfo group may be sodium. The sodium salt of the compound represented by the following formula (7) is, for example, a compound registered under the CAS Registration No. 63870-34-8.

(7)

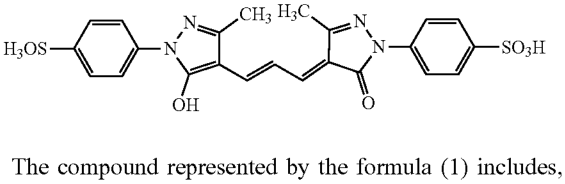

The compound represented by the formula (1) includes, for example, a compound represented by the following formula (8). The compound of the following formula (8) may also be referred to as, for example, 2,4-dihydro-4-[3-(5-hydroxy-1,3-dimethyl-1H-pyrazol-4-yl)-2-propen-1-ylidene]-2,5-dimethyl-3H-pyrazol-3-one. The compound represented by the following formula (8) is, for example, a compound registered under the CAS Registration No. 242129-71-1.

(8)

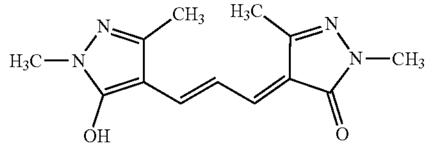

The compound represented by the formula (1) includes, for example, a compound represented by the following formula (9). The compound of the following formula (9) may also be referred to as, for example, 2,4-dihydro-4-[(5-hydroxy-1,3-dimethyl-1H-pyrazol-4-yl) methylene1]-2,5-dimethyl-3H-pyrazol-3-one. Hereinafter, the compound of the following formula (9) is also referred to as BisEp-C1.

(9)

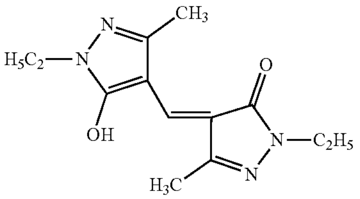

The compound represented by the formula (1) includes, for example, a compound represented by the following formula (10). The compound of the following formula (10) may also be referred to as, for example, Solvent Yellow 93 or 2,4-dihydro-4-[(5-hydroxy-3-methyl-1-phenyl-1H-pyrazol-4-yl)methylene]-5-methyl-2-phenyl-3H-pyrazol-3-one. The compound represented by the following formula (10) is, for example, a compound registered under the CAS Registration No. 4174-09-8.

(10)

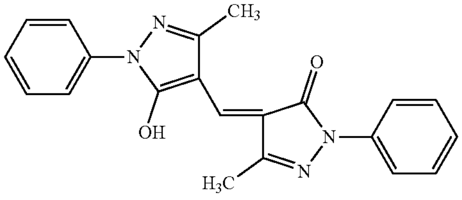

The compound represented by the formula (1) includes, for example, a compound represented by the following formula (11). The compound of the following formula (11) may also be referred to as, for example, 2,4-dihydro-4-[(5-hydroxy-1,3-dimethyl-1H-pyrazol-4-yl) methylene]-2,5-dimethyl-3H-pyrazol-3-one. The compound represented by the following formula (11) is, for example, a compound registered under the CAS Registration No. 151589-04-7.

(11)

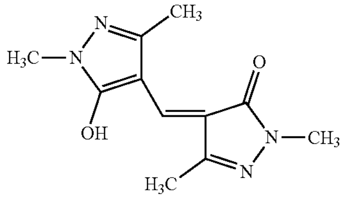

The compound represented by the formula (1) includes, for example, a compound represented by the following formula (12).

(12)

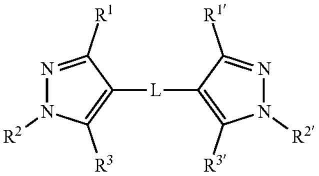

In the formula (12), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^{1'}$ is a hydrogen atom, a halogen atom, or an alkyl group, $R^{2'}$ is an alkyl group or an aryl group that may have a substituent, $R^{3'}$ is a hydrogen atom, a halogen atom, an alkyl group, or a hydroxy group, and L is a saturated or unsaturated hydrocarbon group having 1 to 6 carbon atoms.

In the formula (12), $R^1$ is a hydrogen atom or an alkyl group, $R^2$ is an alkyl group or an aryl group that may have a substituent, $R^3$ is a hydroxy group, $R^{1'}$ is a hydrogen atom or an alkyl group, $R^{2'}$ is an alkyl group or an aryl group that may have a substituent, $R^{3'}$ is an alkyl group or a hydroxy group, and L is preferably a saturated or unsaturated hydrocarbon group having 1 to 6 carbon atoms.

As a specific example, the compound represented by the formula (1) includes, for example, a compound represented by the following formula (13). The compound of the following formula (13) may also be referred to as, for example, 4,4'-methylenebis[1-ethyl-3-methyl-1H-pyrazol-5-ol]. The compound of the following formula (13) is also referred to as BisEp-C1 ($H_2$).

(13)

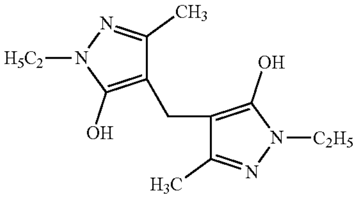

The compound represented by the formula (1) includes, for example, a compound represented by the following formula (14). The compound of the following formula (14) may also be referred to as, for example, 4,4'-methylenebis [3-methyl-1-phenyl-1H-pyrazol-5-ol]. The compound represented by the following formula (14) is, for example, a compound registered under the CAS Registration No. 98395-58-5.

(14)

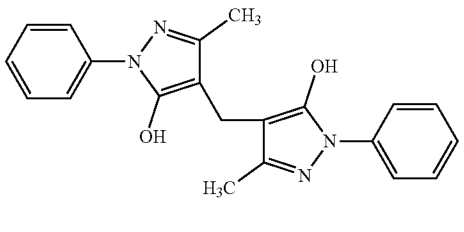

The compound represented by the formula (1) includes, for example, a compound represented by the following formula (15). The compound of the following formula (15) may also be referred to as, for example, 4,4'-methylenebis [1-hexyl-3-methyl-1H-pyrazol-5-ol]. The compound represented by the following formula (15) is, for example, a compound registered under the CAS Registration No. 153231-80-2.

(15)

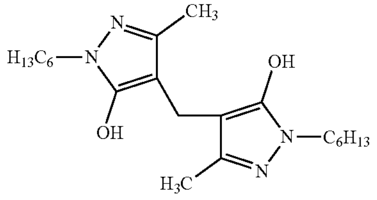

The compound represented by the formula (1) may be, for example, an isomer. The isomer may be, for example, a tautomer or a stereoisomer. The tautomer or stereoisomer may include, for example, all theoretically possible tautomers or stereoisomers. In addition, in the present invention, the configuration of each substituent is not particularly limited. In the vasodilator of the present invention, the compound represented by the formula (1) may be, for example, a hydrate of a compound represented by the formula (1) or a salt thereof, or a solvate.

In the present invention, the salt of the compound represented by the formula (1) is not particularly limited and is, for example, a pharmaceutically acceptable salt. The pharmaceutically acceptable salt is not particularly limited, and examples thereof include alkali metal salts such as sodium salt, potassium salt, and the like; alkaline earth metal salts such as calcium salt, magnesium salt, and the like; ammonium salts; aliphatic amine salts such as trimethylamine salt, triethylamine salt, dichlorohexylamine salt, ethanolamine salt, diethanolamine salt, triethanolamine salt, procaine salt, and the like; aralkylamine salts such as N,N-dibenzylethylenediamine, and the like; heterocyclic aromatic amine salts such as pyridine salt, picoline salt, quinoline salt, isoquinoline salt, and the like; quaternary ammonium salts such as tetramethylammonium salt, tetraethylammonium salt, benzyltrimethylammonium salt, benzyltributylammonium salt, methyltrioctylammonium salt, tetrabutylammonium salt, and the like; amino acid salts such as arginine salt, lysine salt, aspartate salt, glutamate salt, and the like; inorganic acid salts such as hydrochloride, sulfate, nitrate, phosphate, carbonate, bicarbonate, perchlorate, and the like; aliphatic organic acid salts or aromatic organic acid salts such as acetate, propionate, succinate, glycolate, lactate, maleate, fumarate, tartrate, malate, citrate, ascorbate, hydroxymaleate, pyruvate, phenyl acetate, benzoate, 4-aminobenzoate, anthranylate, 4-hydroxybenzoate, salicylate, 4-aminosalicylate, pamoate, gluconate, nicotinate, and the like; and sulfonates such as methane sulfonate, isethionate, ethane sulfonate, benzene sulfonate, halobenzene sulfonate, p-toluene sulfonate, toluene sulfonate, naphthalene sulfonate, sulfanilate, cyclohexyl sulfamate, and the like.

The vasodilator of the present invention may be used, for example, in vivo or in vitro. The vasodilator of the present invention may be composed of, for example, a plurality of components. In this case, the vasodilator of the present invention may also be referred to as a vasodilator composition, for example.

The subject of administration of the vasodilator of the present invention is not particularly limited. When the vasodilator of the present invention is used in vivo, examples of the subject of administration include humans and non-human animals excluding humans. Examples of the non-human animals include mice, rats, rabbits, dogs, sheep, horses, cats, goats, monkeys, and guinea pigs. The subject to be administered may be, for example, a subject with inflammation or a subject with no inflammation. The inflammation means, for example, a condition in which the concentration of inflammatory cytokines such as ROS, TNFα, and the like in blood is significantly higher than that in healthy individuals. When the vasodilator of the present invention is used in vitro, examples of the subject of administration include cells, tissues, and organs, and examples of the cells include cells collected from a living body and cultured cells.

The use condition (administration condition) of the vasodilator of the present invention is not particularly limited, and, for example, an administration form, an administration period, a dosage, and the like can be appropriately determined depending on the type of the subject of administration and the like.

The dosage of the vasodilator of the present invention is not particularly limited. When the vasodilator of the present invention is used in vivo, the dosage can be appropriately determined, for example, depending on the type, symptom, age, administration method, and the like of the subject of administration. As a specific example, when the antioxidant is administered to a human, the dosage of the compound represented by the formula (1) per day in total is, for example, 0.1 to 1,000 mg, 1 to 1,000 mg, 10 to 1,000 mg, or 10 to 100 mg, and preferably 10 to 1,000 mg, 30 to 1,000 mg, 10 to 100 mg, or 30 to 100 mg. The number of administrations per day is, for example, 1 to 5 times, 1 to 3 times, or once or twice, and is preferably 1 to 3 times or once or twice. In the vasodilator of the present invention, the content of the compound represented by the formula (1) is not particularly limited and can be appropriately set according to, for example, the aforementioned dosage per day.

The administration form of the vasodilator of the present invention is not particularly limited. When the vasodilator of the present invention is administered in vivo, it may be administered orally or parenterally. Examples of the parenteral administration include intravenous injection (intravenous administration), intramuscular injection (intramuscular administration), transdermal administration, subcutaneous administration, intradermal administration, enteral administration, rectal administration, vaginal administration, nasal administration, pulmonary administration, intraperitoneal administration, and topical administration.

The dosage form of the vasodilator of the present invention is not particularly limited, and can be appropriately determined depending on, for example, the administration form. Examples of the dosage form include a liquid form and a solid form. Specific examples of the dosage form include preparations for oral administration such as controlled-release formulations (enteric formulation, sustained-release formulation, etc.), capsules, liquids and solutions for oral administration (elixir, suspension, emulsion, aromatic water, lemonade, etc.), syrups (preparation for syrup, etc.), granules (effervescent granule, fine granule, etc.), powders, tablets (orally disintegrating tablet/orodispersible tablet, chewable tablet, effervescent tablet, dispersible tablet, soluble tablet, coated tablet, etc.), pills, jellies for oral administration, and the like; preparations for oro-mucosal application such as tablets for oro-mucosal application (medicated chewing gum, sublingual tablet, troche/lozenge, drop, buccal tablet, mucoadhesive tablet, etc.), sprays for oro-mucosal application, semi-solid preparation for oro-mucosal application, preparation for gargles, and the like; preparations for injection such as injections (implant/pellet, prolonged release injection, parenteral infusion (preparation for infusion), lyophilized injection, powder for injection, prefilled syringe, cartridge, etc.); preparations for dialysis such as dialysis agents (peritoneal dialysis agent and hemodialysis agent) and the like; preparations for inhalation such as inhalations (metered-dose inhaler, inhalation solution, dry powder inhaler, etc.); preparations for ophthalmic application such as ophthalmic ointments, ophthalmic preparations, and the like; preparations for otic application such as ear preparations; preparations for nasal application such as nasal preparations (nasal solution, nasal dry powder inhalers, etc.) and the like; preparations for rectal application such as suppositories for rectal application, semi-solid preparations for rectal application, enemas for rectal application, and the like; preparations for vaginal application such as suppositories for vaginal use, tablets for vaginal use, and the like; and preparations for cutaneous application such as liquids and solutions for cutaneous application (spirit, liniment, lotion, etc.), creams, gels, solid dosage forms for cutaneous application (powder for cutaneous application, etc.), sprays for cutaneous application (aerosol for cutaneous application, pump spray for cutaneous application, etc.), patches (tape/plaster, cataplasm/gel patch, etc.), ointments, and the like. When the vasodilator of the present invention is administered orally, examples of the dosage form include tablets, coated tablets, pills, fine granules, granules, powders, capsules, solutions, syrups, emulsions, and suspensions. When the vasodilator of the present invention is administered parenterally, examples of the dosage form include preparations for injection and preparations for infusion. When the vasodilator of the present invention is administered transdermally, examples of the dosage form include topical agents such as patches, embrocations, ointments, creams, and lotions.

The vasodilator of the present invention may include, for example, an additive if necessary, and when the vasodilator of the present invention is used as a pharmaceutical or a pharmaceutical composition, it is preferred that the additive be a pharmaceutically acceptable additive or includes a pharmaceutically acceptable carrier. The additive is not particularly limited, and examples thereof include a base raw material, an excipient, a colorant, a lubricant, a binder, a disintegrant, a stabilizer, a preservative, and a flavoring agent such as a perfume. In the vasodilator of the present invention, the amount of the additive to be blended is not particularly limited as long as it does not hinder the function of the compound of formula (1).

Examples of the excipient include sugar derivatives such as lactose, sucrose, glucose, mannitol, sorbitol, and the like; starch derivatives such as corn starch, potato starch, a starch, dextrin, and the like; cellulose derivatives such as crystalline cellulose; gum arabic; dextran; organic excipients such as pullulan and the like; silicate derivatives such as light anhydrous silicic acid, synthetic aluminum silicate, calcium silicate, magnesium metasilicate, and the like; phosphates such as calcium hydrogen phosphate and the like; carbonates such as calcium carbonate and the like; and inorganic excipients such as sulfates such as calcium sulfate. Examples of the lubricant include stearic acid metal salts such as stearic acid, calcium stearate, magnesium stearate, and the like; talc; polyethylene glycol; silica; and cure vegetable oil. Examples of the flavoring agent include perfumes such as cocoa powder, menthol, aromatic powder, mint oil, borneol, cinnamon powder, and the like; sweeteners; and acidulants. Examples of the binder include hydroxypropylcellulose, hydroxypropylmethylcellulose, polyvinylpyrrolidone, and macrogol. Examples of the disintegrant include cellulose derivatives such as carboxymethylcellulose, calcium carboxymethylcellulose, and the like; chemically modified starches such as carboxymethylstarch, sodium carboxymethylstarch, cross-linked polyvinylpyrrolidone, and the like; and chemically modified celluloses. Examples of the stabilizer include paraoxybenzoic acid esters such as methyl paraben, propylparaben, and the like; alcohols such as chlorobutanol, benzyl alcohol, phenylethyl alcohol, and the like; benzalkonium chloride; phenols such as phenol, cresol, and the like; thimerosal; dehydroacetic acid; and sorbic acid.

The compounds represented by the formulae (1) to (15) may be commercially available products or may be prepared in-house based on the production examples described below.

The vasodilator of the present invention can scavenge ROS to induce vasodilation as described above. Thus, the vasodilator of the present invention can be used as a pharmaceutical for a disease caused by vascular stenosis, for example, as described below.

<Bloodstream-Improving Agent>

The bloodstream-improving agent of the present invention includes the vasodilator of the present invention as described above. The improving agent of the present invention is characterized in that it includes the vasodilator of the present invention, i.e., a compound represented by the formula (1) or a salt thereof, and other configurations and conditions are not particularly limited. Since the improving agent of the present invention includes the vasodilator of the present invention, ROS can be scavenged, thereby inducing vasodilation. Therefore, the improving agent of the present invention can improve bloodstream to be examined. Regarding the improving agent of the present invention, reference can be made to the description as to the vasodilator of the present invention.

As to the expression "bloodstream improvement" in the present invention, it is acceptable as long as a blood flow is (significantly) increased or raised as compared to the case of absence (non-administration condition) of the improving agent of the present invention, and the blood flow may be decreased or lowered as compared to the initiation (administration initiation). In this case, the "bloodstream improvement" may also be referred to as "suppression of decrease in blood flow," "suppression of blood flow deterioration," or the like, for example. The improvement of bloodstream can be evaluated, for example, based on blood flow of the blood vessel of the subject. The blood flow can be measured by a method using a flow-mediated dilatation (FMD) or second derivative of photoplethysmogram (SDPTG).

The condition for administering the improving agent of the present invention is not particularly limited, and, for example, an administration form, an administration period, a dosage, and the like can be appropriately determined depending on the type of the subject of administration and the like. Regarding the subject and condition of administration of the improving agent of the present invention, reference can be made, for example, to the descriptions as to the subject and condition of administration of the vasodilator of the present invention.

<Vascular Disorder Protective Agent>

A vascular disorder protective agent of the present invention includes the vasodilator according to the present invention as described above. The protective agent of the present invention is characterized in that it includes the vasodilator of the present invention, i.e., a compound represented by the formula (1), and other configurations and conditions are not particularly limited. Since the protective agent of the present invention includes the vasodilator of the present invention, ROS can be scavenged, thereby suppressing vascular endothelial cell damage. Thus, the protective agent of the present invention can protect vascular disorders. For this reason, the protective agent of the present invention can also be referred to as, for example, a suppressor, a prophylactic agent, or an inhibitor of vascular damage or vascular endothelial cell damage, or a suppressor, a prophylactic agent, an inhibitor, or an improving agent of vascular disorder.

In the present invention, "vascular disorder" means, for example, that a blood vessel function is damaged. Specific examples of the "vascular disorder" include blocking or infarction of a blood vessel, breakage of a blood vessel wall, or bleeding associated therewith, and the "vascular disorder" may be used in any sense.

As to the expression "vascular disorder protection" in the present invention, it is acceptable as long as the number of vascular disorders or the frequency of vascular disorder is (significantly) decreased or suppressed as compared to the case of absence (non-administration condition) of the protective agent of the present invention, and the number of vascular disorders or the frequency of vascular disorder may be raised or increased as compared to the initiation (administration initiation). In this case, the "vascular disorder protection" may also be referred to as "suppression of vascular disorder," "suppression of blood flow deterioration," or the like, for example. The protection of vascular disorder can be evaluated, for example, based on blood flow of the blood vessel of the subject. The blood flow can be measured by a method using an FMD or SDPTG.

The condition for administering the protective agent of the present invention is not particularly limited, and, for example, an administration form, an administration period, a dosage, and the like can be appropriately determined depending on the type of the subject of administration and the like. Regarding the subject and condition of administration of the protective agent of the present invention, reference can be made, for example, to the description as to the subject and condition of administration of the vasodilator of the present invention. The protective agent of the present invention can be suitably used, for example, for the protection of vascular disorder in a subject with inflammation.

<Pharmaceutical>

A pharmaceutical for a disease caused by vascular stenosis of the present invention includes the vasodilator of the present invention as described above. The pharmaceutical of the present invention is characterized in that it includes the vasodilator of the present invention, i.e., a compound represented by the formula (1), and other configurations and conditions are not particularly limited. Since the pharmaceutical of the present invention includes the vasodilator of the present invention, ROS generated in vivo can be scavenged, thereby inducing vasodilation. Thus, the pharmaceutical of the present invention can treat a disease caused by vascular stenosis. Regarding the pharmaceutical of the present invention, reference can be made to the descriptions as to the vasodilator, improving agent, and protective agent of the present invention.

The expression "treatment" in the present invention may be used in any sense to suppress or prevent the onset of disease, suppress or stop the progression of disease, suppress or stop the progression of disease symptom, and/or improve disease. Thus, the pharmaceutical of the present invention can also be referred to as, for example, an inhibitor, a prophylactic agent, a progression inhibitor, a progression stopping agent and/or an improving agent. In addition, the pharmaceutical of the present invention is applicable as long as the symptoms or progression of the disease is (significantly) suppressed as compared to the case of absence (non-administration condition) of the pharmaceutical of the present invention, and the disease may be progressed as compared to the initiation (administration initiation).

The term "vascular stenosis" means, for example, that the diameter of a blood vessel to be examined becomes smaller as compared to the blood vessel diameter of a normal blood vessel. The vascular stenosis may include, for example, a state in which the interior of blood vessel is occluded.

The disease caused by the vascular stenosis may be a disease caused only by the vascular stenosis or a disease caused by the vascular stenosis and other causes. Specific examples of the diseases caused by the vascular stenosis include cardiovascular diseases, respiratory system diseases, central nervous system diseases, digestive system diseases, hematological diseases, endocrine system diseases, urological diseases, skin diseases, supporting tissue diseases, eye diseases, tumors, iatrogenic diseases, environmental contamination-induced diseases, and dental diseases.

Examples of cardiovascular diseases include myocardial infarction, arrhythmias, arteriosclerosis, vascular spasm, and ischemia-reperfusion disorder.

Examples of respiratory system diseases include pneumonia, infectious diseases, pulmonary fibrosis due to anti-cancer drugs, adult respiratory distress syndrome (ARDS), paraquat poisoning, disorders caused by smoking, pulmonary emphysema, pulmonary disorders caused by hyperoxia therapy, and respiratory infections such as influenza.

Examples of central nervous system diseases include cerebral edema, cerebral hemorrhage, epilepsy, brain vascular spasm, dementia, depression, autonomic neurological disorder (Reilly phenomena), delayed neuropathy, spinal cord injury, and neurogenic pulmonary edema. Examples of digestive system diseases include acute gastric mucosal disorder, gastric ulcer, ulcerative colitis, Crohn's disease, Behçet's disease, hepatitis, liver cirrhosis, drug-induced liver disorder, liver transplantation disease, various jaundice disease states, and pancreatitis.

Examples of hematological diseases include leukocytic diseases such as chronic granulomatosis, leukemia, acquired immunodeficiency syndrome (AIDS), and sepsis; erythrocytic diseases such as hemoglobinopathies (methemoglobin, thalassemia, sickle cell), hematochromatosis, primaquine hypersensitivity, paroxysmal nocturnal hemoglobinuria, drug-induced anemia, and achatalasemia; and other blood component diseases such as $\alpha_1$-acidity protein disorder, hyperlipidemia, disseminated intravascular coagulation (DIC), and platelet disorder.

Examples of endocrine system diseases include diabetes, adrenal metabolic disorder, and stress reaction. The diabetes may be, for example, a diabetic complication. Examples of the diabetic complication include diabetic neurological disorder ((gastrointestinal disorder constipation/diarrhea), dyshidrosis, orthostatic hypotension, impotence, diabetic autonomic neurological disorder, diabetic muscular atrophy), diabetic retinopathy, diabetic nephropathy, periodontal disease, vascular complicated ischemic heart disease (angina pectoris/myocardial infarction), cerebral infarction arteriosclerosis, skin complication (diabetic necrobiosis lipoidica), diabetic scleredema, granuloma annulare, diabetic xanthoma, Dupuytren's contracture, diabetic foot, skin infections (erysipelas, cellulitis, Cystitis, cutaneous candidiasis, candidal esophagitis, tinea pedis, aspergillosis, fungal infection, etc.)), lower extremity complications (neuropathic arthropathy (Charcot's joint)), diabetic gangrene (toe gangrene), urinary tract infection, and protracted wound healing.

Examples of urological diseases include glomerulonephritis, hemolytic kidney disorder, drug-induced kidney disorder, and disorders caused by anticancer drugs. Examples of skin diseases include burns, sunburns, atopic dermatitis, and skin ulcers.

Examples of supporting tissue system diseases include rheumatoid arthritis, autoimmune disease, and collagen disease.

Examples of eye diseases include retinopathy of prematurity, retinal degeneration, cataract, and corneal ulcer. Examples of the tumor include cancers caused by smoking, chemical carcinogenesis or disorders caused by cancer chemotherapy, radiation disorder or disorders caused by radiation therapy, and an oral cancer.

Examples of iatrogenic diseases include a drug use disorder, disorders caused by an anticancer drug (leukopenia, etc.), bleomycin pulmonary fibrosis, adriamycin cardiomyopathy, cisplatin kidney disorder, and phototherapy (photosensitizer).

Examples of environmental contamination-induced diseases include disorders caused by heavy metals, Minamata disease, asthma, exhaust gas pulmonary disorders, and various poisonings caused by water pollution.

Examples of dental diseases include periodontal disease, temporomandibular joint disease, xerostomia, and oral mucosal disease (stomatitis).

The condition for administering the pharmaceutical of the present invention is not particularly limited, and, for example, an administration form, an administration period, a dosage, and the like can be appropriately determined depending on the type of the subject of administration and the like. Regarding the subject and condition of administration of the pharmaceutical of the present invention, reference can be made, for example, to the description as to the subject and condition of administration of the vasodilator of the present invention.

A pharmaceutical of the present invention includes the vascular disorder protective agent of the present invention. Thus, the pharmaceutical of the present invention may be used as a pharmaceutical for a disease caused by vascular disorder, for example. The disease caused by the vascular disorder may be a disease caused only by the vascular disorder, or may be a disease caused by the vascular disorder and other causes. As a specific example, regarding the diseases caused by vascular disorder, reference can be made to the examples of the disease caused by vascular stenosis, for example.

The pharmaceutical of the present invention may be administered to, for example, a patient diagnosed with vascular stenosis or a patient diagnosed with vascular disorder.

<Vasodilation Method>

The vasodilation method of the present invention uses the vasodilator of the present invention, as described above. The vasodilation method of the present invention is characterized in that it uses the vasodilator of the present invention, i.e., a compound represented by the formula (1) or a salt thereof, and other steps and conditions are not particularly limited. Since the vasodilation method of the present invention uses the vasodilator of the present invention, ROS can be scavenged, thereby inducing vasodilation. Regarding the vasodilation method of the present invention, reference can be made to the description as to the vasodilator of the present invention.

The vasodilation method of the present invention includes the step of administering the vasodilator of the present invention, for example. Specifically, the vasodilation method of the present invention includes the step of administering to a subject of administration the vasodilator. The vasodilator may be administered in vitro or in vivo. Regarding the subject and condition of administration of the vasodilator of the present invention, reference can be made, for example, to the description as to the subject and condition of administration in the vasodilator or the protective agent of the present invention.

<Bloodstream-Improving Method>

The bloodstream-improving method (hereinafter also referred to as "improving method") of the present invention uses the bloodstream-improving agent of the present invention. The improving method of the present invention is characterized in that it uses the improving agent of the present invention, i.e., a compound represented by the formula (1) or a salt thereof, and other steps and conditions are not particularly limited. Since the improving method of the present invention uses the improving agent of the present invention, ROS can be scavenged, thereby inducing vasodilation. Thus, the improving method of the present invention can improve the bloodstream. Regarding the improving method of the present invention, reference can be made to the descriptions as to the vasodilator, protective agent, and improving agent of the present invention described above.

The improving method of the present invention includes the step of administering the improving agent of the present invention, for example. Specifically, the improving method of the present invention includes the step of administering to a subject of administration the improving agent. The improving agent may be administered in vitro or in vivo. Regarding the subject and condition of administration of the improving agent of the present invention, reference can be made, for example, to the description as to the subject and condition of administration of the vasodilator or the protective agent of the present invention.

<Vascular Disorder Protection Method>

The vascular disorder protection method (hereinafter also referred to as "protection method") of the present invention uses the vascular disorder protective agent of the present invention. The protection method of the present invention is characterized in that it uses the vascular disorder protective agent of the present invention, i.e., a compound represented by the formula (1) or a salt thereof, and other steps and conditions are not particularly limited. Since the protection method of the present invention uses the protective agent of the present invention, ROS can be scavenged, thereby protecting from vascular disorder. Regarding the protection method of the present invention, reference can be made to the descriptions as to the vasodilator, improving agent, and protective agent of the present invention described above.

The protection method of the present invention includes the step of administering the protective agent of the present invention, for example. Specifically, the protection method of the present invention includes the step of administering to a subject of administration the protective agent. The protective agent may be administered in vitro or in vivo. Regarding the subject and condition of administration of the protective agent of the present invention, reference can be made, for example, to the description as to the subject and condition of administration of the vasodilator or the protective agent of the present invention.

<Treatment Method of Disease Caused by Vascular Stenosis>

A method for treating a disease caused by vascular stenosis of the present invention (hereinafter also referred to as "treatment method") includes the step of administering to a patient the pharmaceutical of the present invention. The treatment method of the present invention is characterized in that it administrates the pharmaceutical of the present invention, i.e., a compound represented by the formula (1) or a salt thereof, and other steps and conditions are not particularly limited. Since the treatment method of the present invention uses the pharmaceutical of the present invention described above, ROS generated in vivo can be scavenged, thereby dilating blood vessels. Thus, the treatment method of the present invention can treat a disease caused by vascular stenosis. Also, since the treatment method of the present invention uses the pharmaceutical of the present invention described above, a subject can be protected from vascular disorders caused in vivo. Thus, the treatment method of the present invention can treat a disease caused by a vascular disorder. Regarding the treatment method of the present invention, reference can be made to the descriptions as to the vasodilator, improving agent, protective agent, pharmaceutical, and vasodilation method of the present invention.

The treatment method of the present invention includes the step of administering the pharmaceutical of the present invention, for example. Specifically, the treatment method of the present invention includes the step of administering to a patient the pharmaceutical. The pharmaceutical may be administered in vitro or in vivo. Regarding the subject and condition of administration of the pharmaceutical of the present invention, reference can be made, for example, to the description as to the subject and condition of administration in the vasodilator or protective agent of the present invention. The patient may be a patient suffering from the aforementioned disease, a patient predicted to suffer from the disease, or a patient unknown whether to suffer from the disease. The patient may be a patient with a disorder caused by the vascular stenosis or vascular disorder, a patient predicted to suffer from a disorder caused by the vascular stenosis or vascular disorder, or a patient unknown whether to suffer from a disorder caused by the vascular stenosis or vascular disorder.

As described above, the pharmaceutical of the present invention can protect vascular disorders. Thus, the treatment method of the present invention can be used for treating a disease caused by vascular disorder.

<Use of Compound or Salt thereof>

The present invention is the use of a compound represented by the formula (1) or a salt thereof for use in vasodilation, bloodstream improvement, or vascular disorder protection, and the use of a compound represented by the formula (1) or a salt thereof for use in treatment of a disease caused by vascular stenosis or vascular disorder. In addition, the present invention is the use of a compound represented by the formula (1) or a salt thereof for producing a vasodilator, a bloodstream-improving agent, or a vascular disorder protective agent, and the use of a compound represented by the formula (1) or a salt thereof for producing a pharmaceutical for a disease caused by vascular stenosis or vascular disorder. Regarding the use of the present invention, reference can be made, for example, to the descriptions as to the vasodilator, improving agent, protective agent, pharmaceutical, vasodilation method, improving method, and protection method of the present invention.

EXAMPLES

Next, examples of the present invention will be described. The present invention, however, is not limited by the following examples. Commercially available reagents were used based on their protocols unless otherwise mentioned.

Example 1

A compound included in the vasodilator of the present invention was synthesized.

(1) Synthesis of ED2AP 3.58 g of 3-methyl-1-phenyl-5-pyrazolone (hereinafter also referred to as "edaravone"), 2.59 g of malonaldehyde dianilide hydrochloride, and 20 ml of ethanol were added to a reactor and dissolved. To the obtained solution, 2.04 g of triethylamine and 0.4 ml of water were added and stirred for 1 hour at room temperature (about 25° C.; hereinafter, the same applies). After the stirring, the resultant was further reacted for 1 hour at 50° C. After discharging the obtained reaction solution to 100 ml of 1N hydrochloric acid, the mixture was sufficiently stirred and the precipitate was filtered. The resulting cake was washed with water. The cake was added to 200 ml of an aqueous sodium hydroxide solution having a 1% by weight concentration and completely dissolved by heating with stirring. Next, the dissolved solution was stirred for 3 hours after cooling to room temperature. Then, the liquid containing the obtained precipitate was filtered, and then the cake was washed with water. This resulted in 2.99 g of dark red crystal of ED2AP having the following physical properties. Note that the melting point of ED2AP was 249° C., which was water-soluble.

$^1$H-NMR (nuclear magnetic resonance) (600 MHz, Internal Standard: THF (tetrahydrofuran)-d8, AV-600 (Bruker)): δ2.33 (s, 6H), 6.92 (d, 2H), 7.02 (m, 2H), 7.21 (m, 4H), 8.01 (m, 4H), 8.31 (t, 1H)

(2) Synthesis of Compound of Formula (10)

3 ml of dimethylformamide was added to a reactor and the exterior of the reactor was cooled with ice water. 1.75 g of phosphorus oxychloride was slowly dropped into the reactor (Reaction Solution A). In another reactor, 1.78 g of edaravone was dissolved in 5 ml of dimethylformamide (Reaction Solution B). Under room temperature, the reaction solution B was slowly added to the reaction solution A, and the resulting mixture was allowed to react for 1 hour with the end of addition (Reaction Solution C) being a reference. In another reactor, 1.81 g of 3-methyl-1-phenyl-5-pyrazolone was added to 8 ml of chloroform and dissolved (Reaction Solution D). Under room temperature, the Reaction Solution C was slowly added to the Reaction Solution D, followed by stirring for 20 minutes and further stirring at 70° C. for 1 hour. To the resultant, 0.2 g of water was added and stirred for another 2 hours. The obtained reaction solution was discharged into 100 ml of water and extracted with a mixed solvent of toluene/ethyl acetate=1/1 (volume ratio). After condensation of the obtained extract, column purification was performed to obtain 2.92 g of yellow crystal of the compound of the formula (10) having the following physical properties. Note that the melting point of the compound of the formula (10) was 177° C., which was poorly soluble in water.

$^1$H-NMR (nuclear magnetic resonance) (600 MHZ, Internal Standard: $CDCl_3$, AV-600 (Bruker)): δ2.33 (s, 6H), 7.20 (s, 1H), 7.26 (m, 2H), 7.43 (m, 4H), 7.90 (dd, 4H)

(3) Synthesis of Compound of Formula (14)

1.00 g of edaravone, 0.72 g of paraformaldehyde, and 20 ml of formic acid were added to a reaction flask and stirred overnight for 20 hours at 70° C. The obtained reaction solution was discharged into 80 ml of water and extracted with a mixed solvent of toluene/ethyl acetate=1/1 (volume ratio). When the extract was condensed to about two-thirds, crystals were precipitated. Further, the resultant was cooled to room temperature, and sufficiently crystallized, and then filtered. The obtained cake was washed with toluene to obtain 0.88 g of pale yellow crystal of the compound of the formula (14) having the following physical properties. Note that the compound of the formula (14) was poorly soluble in water.

$^1$H-NMR (nuclear magnetic resonance) (600 MHz, Internal Standard: DMSO (dimethylsulfoxide)-d6, AV-600 (Bruker)): δ62.31 (s, 6H), 3.43 (s, 2H), 7.32 (m, 2H), 7.48 (m, 4H), 7.70 (m, 4H)

(4) Synthesis of BisEp-C3

In Example 1(1), synthesis was performed in the same manner as described above except that 3-methyl-1-ethyl-5-pyrazolone was used instead of edaravone to obtain red crystal of BisEp-C3 having the following physical properties. Note that BisEp-C3 was water-soluble.

$^1$H-NMR (nuclear magnetic resonance) (600 MHZ, DMSO (dimethylsulfoxide)-d6, AV-600 (Bruker)): δ1.18 (t, 6H), 2.19 (s, 6H), 3.69 (q, 4H), 7.29 (d, 2H), 8.00 (t, 1H)

(5) Synthesis of BisEp-C1

In Example 1(2), synthesis was performed in the same manner as described above except that 3-methyl-1-ethyl-5-pyrazolone was used instead of edaravone to obtain yellow crystal of BisEp-C1 having the following physical properties. Note that BisEp-C1 was water-soluble.

$^1$H-NMR (nuclear magnetic resonance) (600 MHz, DMSO (dimethylsulfoxide)-d6, AV-600 (Bruker)): δ1.24 (t, 6H), 2.23 (t, 6H), 3.79 (q, 4H), 7.33 (s, 1H)

(6) Synthesis of BisEp-C1 ($H_2$)

In Example 1(3), synthesis was performed in the same manner as described above except that 3-methyl-1-ethyl-5-pyrazolone was used instead of edaravone, then the obtained reaction solution was condensed, and the resultant was subjected to column purification to obtain colorless crystal of BisEp-C1 ($H_2$) having the following physical properties. Note that BisEp-C1 ($H_2$) was water-soluble.

$^1$H-NMR (nuclear magnetic resonance) (600 MHz, DMSO (dimethylsulfoxide)-d6, AV-600 (Bruker)): δ1.18 (t, 6H), 2.09 (t, 6H), 3.04 (s, 2H), 3.73 (q, 4H)

Example 2

It was examined that the decomposition of the vasodilator of the present invention in water and an aqueous solvent is suppressed, that is, the antioxidant of the present invention has storage stability.

The storage stability of edaravone, EMPO, ED2AP, and BisEp-C3 of the following formula (A) were examined. Specifically, edaravone, EMPO, ED2AP, and BisEp-C3 were dissolved in pH7.4-PBS or pure water so as to have a final concentration of 200 μmol/1 to prepare dissolved solutions of these compounds. When the compounds were difficult to be dissolved, they were dissolved in an ultrasonic cleaner with warm water at 40° C.

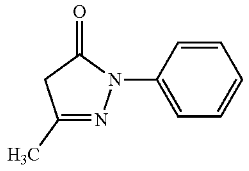

Edaravone

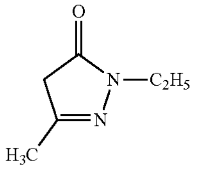

EMPO

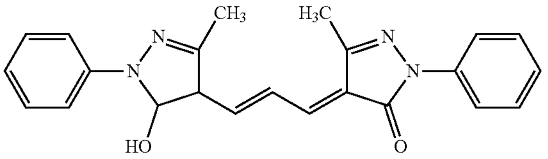

ED2AP

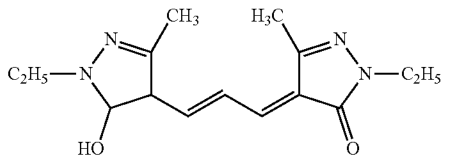

BisEp-C3

Under the measurement conditions for High-Performance Liquid Chromatography (HPLC) described below, the initial concentration was quantified, and then each solution was stored in an oven, which was protected from light, at 37° C., and quantified under the same measurement conditions after 1 week and 2 weeks, to determine residual rate (%) with the initial concentration (100%) being a reference. The results are summarized in Table 1 below.

Measurement Conditions for HPLC

Equipment:

High-Performance Liquid Chromatography (Shimadzu Corporation)

Data-processing software (Model: LCsolution Ver. 1.0, produced by Shimadzu Corporation)

Pump (Model: LC-20AD; produced by Shimadzu Corporation)

Column oven (Model: CTO-20A; produced by Shimadzu Corporation)

Autosampler (Model: SIL-20A; produced by Shimadzu Corporation)

PDA detector (Format: SPD-M20A)

HPLC Assay Conditions:

Column: Atlantis dC18 5 μm (250×4.6 mm I.D.; produced by Waters)

Column temperature: 45° C.

Flow rate: 0.5 ml/min

Detection method: UV (254 nm)

Eluate A: pH3 buffer solution (adjusted to pH3 by adding phosphoric acid to 0.05M $KH_2PO_4$ aqueous solution)/methanol=90/10

Eluate B: methanol

Eluate C: acetonitrile

Time Program (gradient):

| Time (min) | 0 | 10 | 20 | 45 | 70 |
|---|---|---|---|---|---|
| Eluate A (%) | 100 | 100 | 80 | 30 | 30 |
| Eluate B (%) | 0 | 0 | 20 | 20 | 20 |
| Eluate C (%) | 0 | 0 | 0 | 50 | 50 |

TABLE 1

| | | Residual rate (%) | | |
|---|---|---|---|---|
| Solution | Substance name | Initial concentration | After 1 week | After 2 weeks |
| pH 7.4-PBS | Edaravone | 100 | 31.2 | 0.2 |
| | EMPO | 100 | 0.0 | 0.0 |
| | ED2AP | 100 | 96.2 | 91.3 |
| | BisEp-C3 | 100 | 98.7 | 93.6 |
| Pure water | Edaravone | 100 | 82.8 | 80.4 |
| | EMPO | 100 | 6.3 | 1.4 |
| | ED2AP | 100 | 96.1 | 89.8 |
| | BisEp-C3 | 100 | 99.4 | 88.5 |

As summarized in Table 1, it was found that ED2AP and BisEp-C3 have a higher residual rate and excellent storage stability as compared to edaravone and EMPO in both the cases of storing in pure water and a phosphate buffer. In particular, ED2AP and BisEp-C3 have extremely high storage stability in a phosphate buffer as compared to edaravone and EMPO, which shows that they are suitable as pharmaceuticals to be stored in aqueous solvents.

This showed that the decomposition of the vasodilator of the present invention in water and an aqueous solvent is suppressed, that is, the antioxidant of the present invention has storage stability.

Example 3

It was examined that the vasodilator of the present invention has an eliminating ability for non-radical species such as singlet oxygen before and after storage in an aqueous solvent.

The ESR method was used to track changes in singlet oxygen-eliminating ability in PBS solutions of edaravone, EMPO, ED2AP, and BisEp-C3. Specifically, the following reaction system was utilized. First, PBS solutions containing Pterin-6-carboxylic acid (30 μmol/l) and 4-oxo-TEMP (4 mmol/l) are irradiated with a 200 W mercury xenon lamp (hv, RUVF-203S) for 5 seconds using a band-pass filter of 340 nm. Then, in the reaction system, singlet oxygen ($^1O_2$) is generated by the following actions.

Pterin-6-carboxylic acid+hv →Pterin-6-carboxylic acid*

Pterin-6-carboxylic acid*+$^3O_2$→Pterin-6-carboxylic acid+$^1O_2$

Next, the resulting singlet oxygen reacts with 4-oxo-TEMP added to the reaction system as shown in the following formula (B), resulting in a nitroxide that is a stable radical detectable by ESR. This radical causes a triplet derived from N (nitrogen atom) in the ESR spectrum as shown in (A) in FIG. 1.

[formula B]

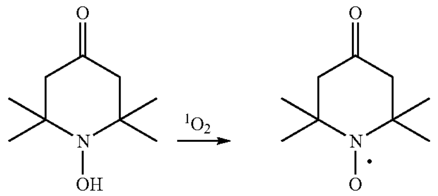

4-Oxo-2,2,6,6-tetramethylpiperidine (4-oxo-TEMP)

4-Oxo-2,2,6,6-tetramethylpiperidine-N-oxyl (4-oxo-TEMPO) Stable radical

When edaravone, EMPO, ED2AP, or BisEp-C3 is added to the reaction system, the intensity of the signal obtained by ESR changes. Thus, the singlet oxygen-eliminating ability of each compound can be examined based on the following formula (C).

[formula C]

$$O_2^3 \xrightarrow{hv} O_2^1$$

$$O_2^1 + \text{4-oxoTEMP} \xrightarrow{k_1} \text{4-oxoTEMPO (Observable by ESR)}$$

$$O_2^1 + \text{Evaluation reagent} \xrightarrow{k_2} \text{Product not observed by ESR}$$

$$-d[\text{4-oxoTEMP}]/dt = d[\text{4-oxo-TEMPO}]/dt = k_1[\text{4-oxoTEMP}][O_2^1]$$

$$-d[\text{Evaluation reagent}]/dt = d[\text{Product}]/dt = k_2[\text{Evaluation reagent}][O_2^1]$$

$I_0$: 4-oxo-TEMPO signal intensity obtained without antioxidant

I: 4-oxo-TEMPO signal intensity obtained when evaluation reagent is added

I: Proportional to amount of 4-oxo-TEMPO $I_0$-I: Proportional to product not observed by ESR $(I_0-I)/I = k_2[\text{Evaluation reagent}][O_2^1]/k_1[\text{4-oxoTEMP}][O_2^1]$ $[\ ]_0$: Concentration at start of reaction $(I_0-I)/I = k_2/k_1 * [\text{Evaluation reagent}]_0/[\text{4-oxoTEMP}]_0$ The prepared PBS solutions of edaravone, EMPO, ED2AP, and BisEp-C3 were stored and examined for the singlet oxygen-eliminating ability over time in the same manner as in Example 2. The ESR measurement conditions 1 were as follows. In addition, the singlet oxygen-eliminating ability was calculated as a relative value with the eliminating ability at day 0 being a reference.

ESR Measurement Conditions 1

Equipment:

Electron spin resonance spectrometer (JES-TE-300; produced by Japan Electron Optics Laboratory Co. Ltd.)

Measurement conditions:

Microwave output: 8 mW

Sweep time: 1 minute

Sweep width: 335.5±5 mT

Magnetic field modulation: 100 kHz 0.079 mT

Gain: ×630

Time constant: 0.03 sec

Figure 1B:
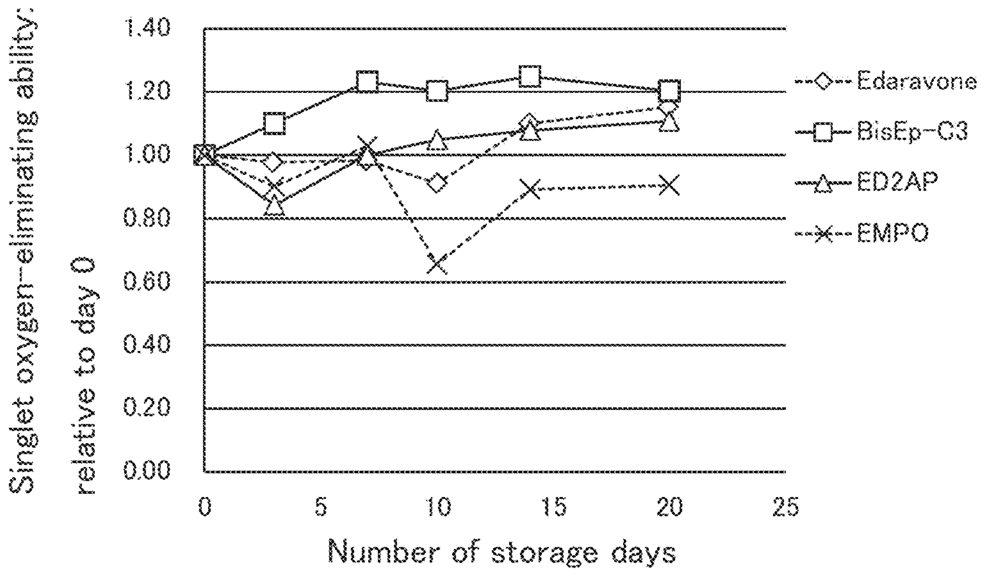

The results are shown in FIG. 1, which displays graphs showing ESR results. In FIG. 1, (A) is a graph showing a triplet derived from N (nitrogen atom) in the ESR spectrum and (B) is a graph showing the results of ESR of each compound. In (B) of FIG. 1, the horizontal axis indicates the number of storage days and the vertical axis indicates the relative value of the singlet oxygen-eliminating ability with the start of storage (day 0) being 1. As shown in (B) of FIG. 1, for any of the compounds, the singlet oxygen-eliminating ability after storage did not differ greatly from that at the start of storage. These results showed that the vasodilator of the present invention had an eliminating ability for a non-radical species such as singlet oxygen before and after storage in an aqueous solvent. These results also suggested that the products of edaravone and EMPO after decomposition have the singlet oxygen-eliminating ability.

Example 4

It was examined that the vasodilator of the present invention has an eliminating ability for radical species such as superoxide anion.

For examining the reactive oxygen-eliminating effect of the vasodilator of the present invention, the superoxide produced by the neutrophils when the neutrophils isolated from the peripheral blood of healthy individuals were stimulated with PMA (phorbor-12-myristate-13-acetate) was used. The superoxide production amount was measured by chemiluminescence using CLA (2-methyl-6-phenyl-3, 7-dihydroimidazo[1,2-α]pyrazine-3-one).

First, ED2AP, BisEp-C3, edaravone, BisEp-C1, or BisEp-C1 ($H_2$) was added to a neutrophil of $4\times10^5$ cells per sample so as to achieve a predetermined concentration (0, 12.5, 25, 50, 100, or 200 μmol/1, or 0, 125, 250, 500, 1,250, 2,500 or 5,000 μmol/1) with 5 μmol of CLA, and then the cell suspension was seeded in flat-bottomed 96-well plates. The volume of the suspension was 200 μl/well, and phenol red-free Ca+, Mg+ HBSS was used as the solution. In addition, the neutrophil was stimulated by adding PMA so as to achieve a concentration of 100 ng/ml. After the stimulation, a plate reader (Envision 2104 Multilabel Reader produced by Perkin Elmer Co., Ltd.) was used to measure the chemiluminescence value over time for 30 minutes with the PMA stimulation time being a reference. The measurement interval was 30 seconds. The sum of the chemiluminescence values obtained every 30 seconds for 30 minutes was taken as the superoxide production amount. In addition, as a control, the superoxide production amount was measured in the same manner except that each compound was not added. The relative value of the superoxide production amount when each compound was added was calculated with the superoxide production amount of the control being 100. The results are shown in FIG. 2.

Figure 2A:
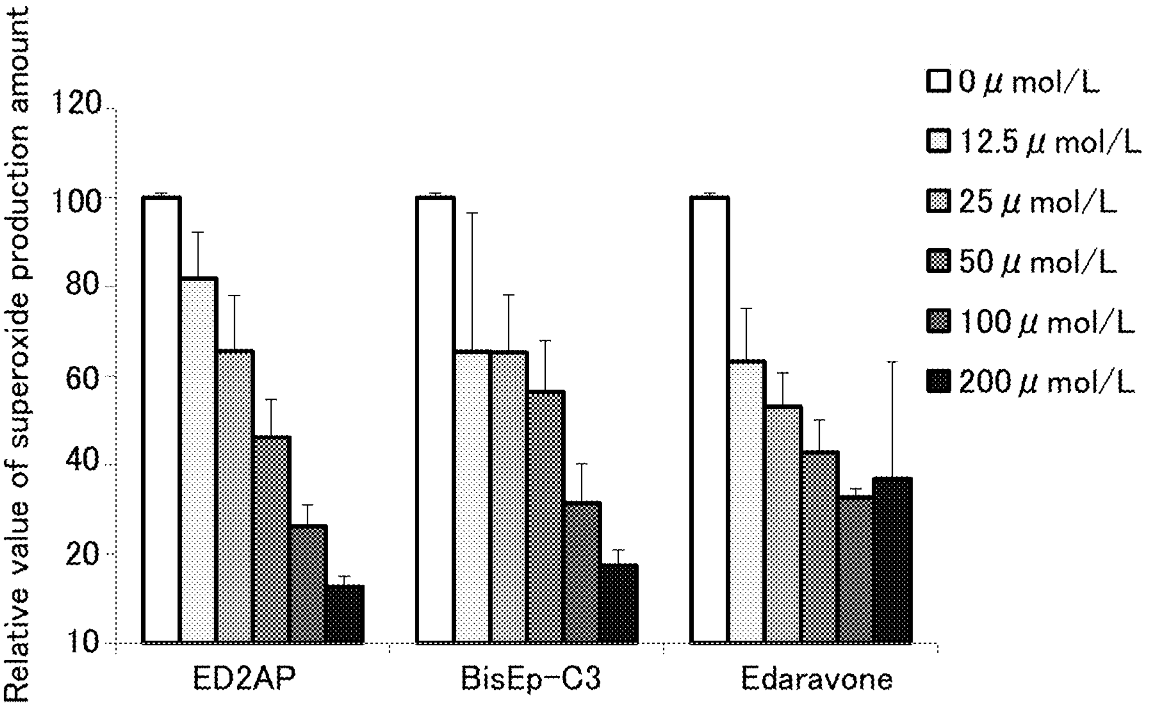
FIG. 2 shows graphs showing the relative value of the superoxide production amount in Example 4.
Figure 2B:
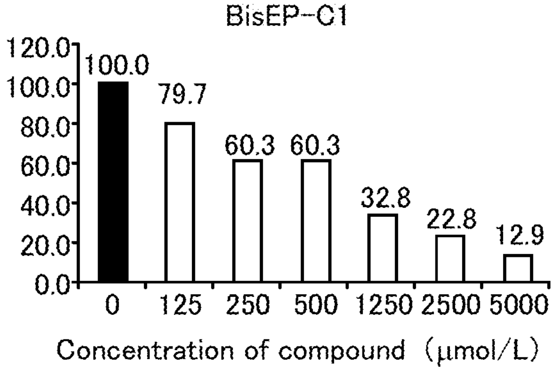
Figure 2C:
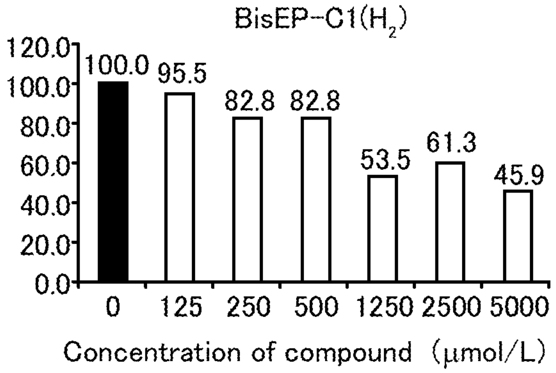

FIG. 2 shows graphs displaying the relative values of the superoxide production amount. In FIG. 2, (A) is a graph showing the results of ED2AP, BisEp-C3, and edaravone, (B) is a graph showing the results of BisEp-C1, and (C) is a graph showing the results of BisEp-C1 ($H_2$). In FIG. 2, the horizontal axis indicates the type of the compound or the concentration of the compound, and the vertical axis indicates the relative value of the superoxide production amount. As shown in FIGS. 2A to 2C, all of the compounds suppressed the superoxide production amount in a concentration-dependent manner, i.e., showed the ROS-eliminating ability. Among the above compounds, ED2AP and BisEp-C3 remarkably suppressed superoxide production amount, and the ROS-eliminating ability is more potent than edaravone at high concentrations. These results showed that the vasodilator of the present invention has an eliminating ability for radical species such as superoxide anion.

Example 5

It was examined that the vasodilator of the present invention alleviates the cytotoxicity of the ROS, that is, has a cytoprotective function.

Edaravone, ED2AP and BisEp-C3 were examined for whether they had the function of alleviating neuronopathy. Specifically, singlet oxygen was generated by combining Rose Bengal (RB), which is a sensitizer, with green light (G-LED), and the function of alleviating the cytotoxicity of the generated singlet oxygen was examined with the cellular activity being an indicator.

First, rat neuroid cells B50 were cultured in 12-well dishes at $2\times10^5$ cells/well (medium: RPMI-1640 medium containing 5% FCS) overnight. After the culturing, the medium of each well was replaced with HBSS (1,000 μl/well; phenol red-free Ca+, Mg+) containing 200 nmol/1 RB and edaravone, ED2AP, or BisEp-C3 having a predetermined concentration (0, 12.5, 25, 50, or 100 μmol/1). The dish was then irradiated with G-LED for 5 minutes to generate singlet oxygen. Thereafter, the medium of each well was replaced with 1,000 μl of HBSS, and Alamar Blue was added. The dish was then allowed to react for about 2 hours in an incubator at 37° C. and 5%$CO_2$. After the reaction, fluorescence intensity (excitation wavelength: λ-560 nm, fluorescence wavelength: λ-595 nm) was measured with a plate reader (infinite200, Tecan Trading AG). In this experimental system, the higher the cellular activity, the more Alamar Blue is taken up and the higher the fluorescence intensity. As a control, fluorescence intensity was measured in the same manner except that sodium azide (Azide, $NaN_3$) was added instead of the compounds so as to achieve a concentration of 4 mmol/1. As a negative control (NC), fluorescence intensity was measured in the same manner except that RB was not added. The relative value of the fluorescence intensity in the sample to which each compound was added was calculated with the fluorescence intensity of the negative control being 100. The results are shown in FIG. 3.

Figure 3:
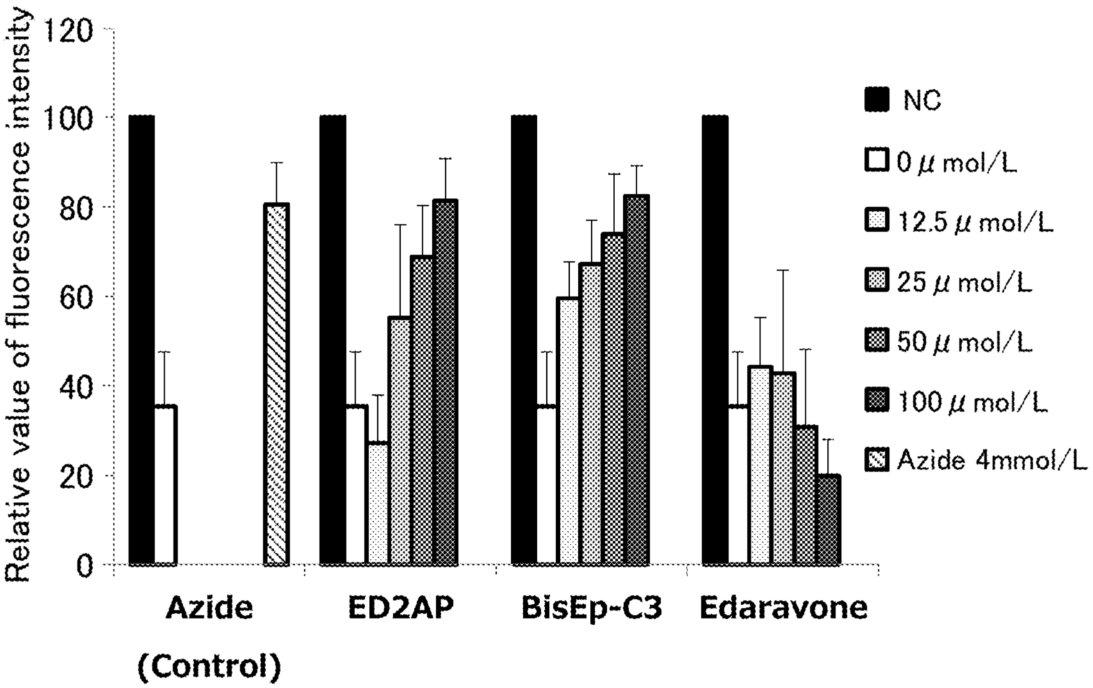
FIG. 3 is a graph showing the relative value of the fluorescence intensity in Example 5.

FIG. 3 is a graph showing the relative value of the fluorescence intensity. In FIG. 3, the horizontal axis indicates the type of the compound or the concentration of the compound, and the vertical axis indicates the relative value of the fluorescence intensity. As shown in FIG. 3, when the fluorescence intensity of the sample subjected to only G-LED irradiation without adding RB was set to 100, in the sample to which RB was added and subjected to G-LED irradiation, cell death due to the generated singlet oxygen is induced, and its fluorescence intensity was reduced to 33.17 (control). On the other hand, when sodium azide (Azide) having a singlet oxygen-eliminating effect was added, the fluorescence intensity was recovered to 80.81. When ED2AP and BisEp-C3 were added, the fluorescence intensity was recovered in a concentration-dependent manner. In contrast, the fluorescence intensity was not recovered in edaravone. These results showed that the vasodilator of the present invention alleviates the cytotoxicity of the ROS, that is, has a cytoprotective function. Furthermore, it was found that the cytoprotective function of ED2AP and BisEp-C3 was higher than that of edaravone.

Example 6

It was examined that the vasodilator of the present invention has an eliminating ability for radical species such as superoxide before and after storage in an aqueous solvent.

PBS solutions of ED2AP, BisEp-C3, and edaravone were prepared in the same manner as in Example 2 and stored for 10 days. The superoxide production amount was calculated in the same manner as in Example 4 except that the PBS solution after storage was added instead of ED2AP, BisEp-C3, edaravone, BisEp-C1 or BisEp-C1 ($H_2$) so as to achieve a predetermined concentration (0, 6.25, 12.5, 25, 50, 100 or 200 μmol/1) of ED2AP, BisEp-C3 or edaravone. Further, PBS solutions of ED2AP, BisEp-C3, and edaravone were prepared in the same manner as in Example 2, and the superoxide production amount was calculated in the same manner except that the PBS solution immediately after preparation was used. Then, the relative value of the superoxide production amount of each sample was calculated with the superoxide production amount of the sample of 0 μmol/1 being 100. The results are shown in FIG. 4.

Figure 4A:
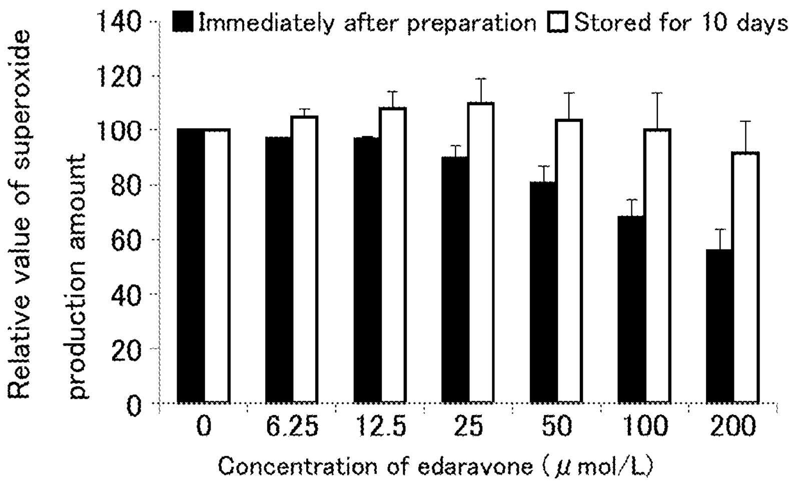
FIG. 4 shows graphs showing the relative value of the superoxide production amount in Example 6.
Figure 4B:
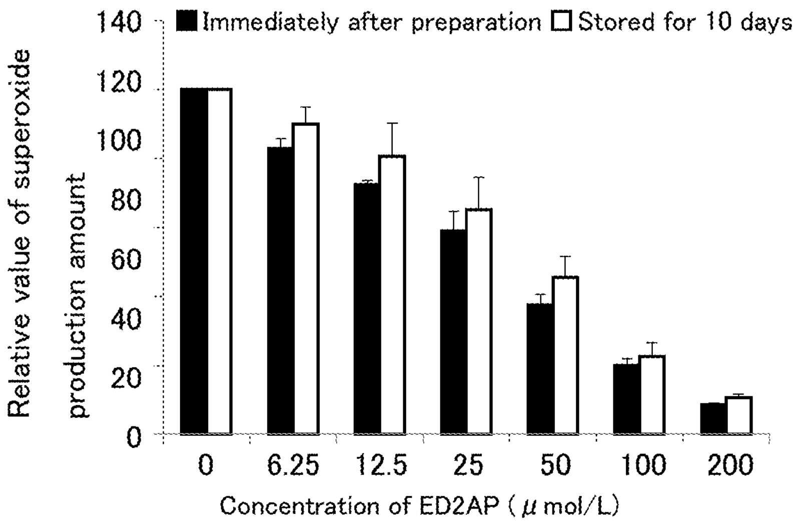
Figure 4C:
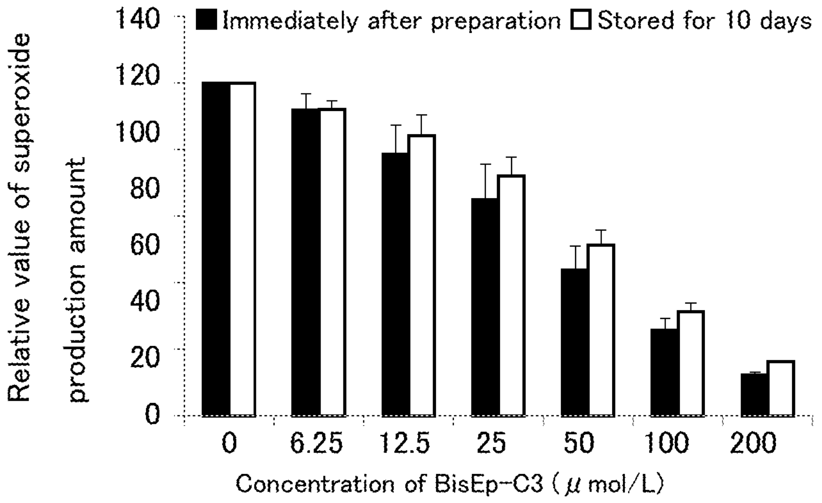

FIG. 4 shows graphs displaying the relative value of the superoxide production amount. In FIG. 4, (A) shows the result of edaravone, (B) shows the result of ED2AP, and (C) shows the result of BisEp-C3. As shown in (A) in FIG. 4, the superoxide-eliminating ability of edaravone was remarkably lowered after storage for 10 days. In contrast, ED2AP and BisEp-C3 maintained the superoxide-eliminating ability equivalent to that immediately after preparation even after storage. This showed that the vasodilator of the present invention has an eliminating ability for radical species such as superoxide before and after storage in an aqueous solvent.

Example 7

It was examined that the vasodilator of the present invention has low cytotoxicity and that the byproduct obtained after reacting the vasodilator of the present invention with singlet oxygen has low cytotoxicity.

(1) Toxicity Evaluation

Rat neuroid cells B50 were seeded in 12-well plates and then cultured. Edaravone (RC), ED2AP, or BisEp-C3 was added to each well so as to achieve a predetermined concentration (12.5, 25, 50, 100, or 200 μmol/1), and then incubated for 24 hours at 37° C. and 5% $CO_2$. Cell viability in each well after the culture was measured using Alamar Blue. The results are shown in FIG. 5.

Figure 5:
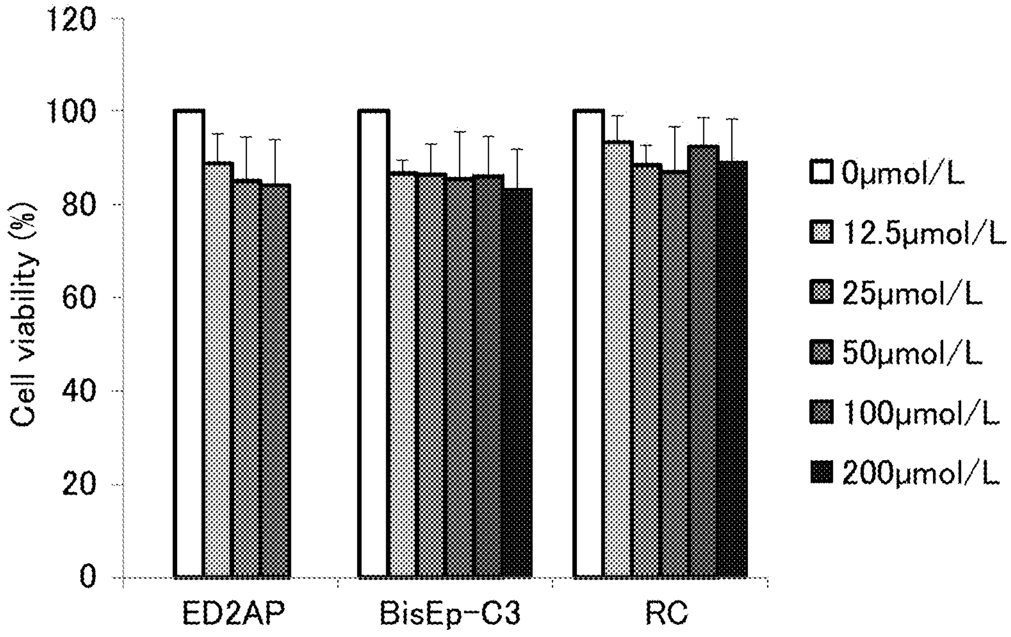
FIG. 5 is a graph showing the cell viability in Example 7.

FIG. 5 is a graph showing the cell viability. In FIG. 5, the horizontal axis indicates the type of the compound or the concentration of the compound, and the vertical axis indicates the cell viability. As shown in FIG. 5, edaravone, ED2AP, and BisEp-C3 were not cytotoxic at any concentration.

(2) Toxicity Evaluation on Byproducts

In a cell-free system, the RB was added to media (5% FCS-containing RPMI-1640 media) containing edaravone, ED2AP, and BisEp-C3 having a predetermined concentration (50, 100, or 200 μmol/1) and then irradiated with LED (G-LED) at 525 nm to generate singlet oxygen, whereby reacting each compound with singlet oxygen. The cell viability was measured in the same manner as in Example 7(1), except that the culture solution after the reaction was used as a medium of the neuroid cell B50. As a negative control (NC), the cell viability was measured in the same manner except that each compound and PB were not added in the cell-free system. Further, as a control (RB), the cell viability was measured in the same manner except that each compound was not added and only PB was added in the cell-free system. The results are shown in FIG. 6.

Figure 6:
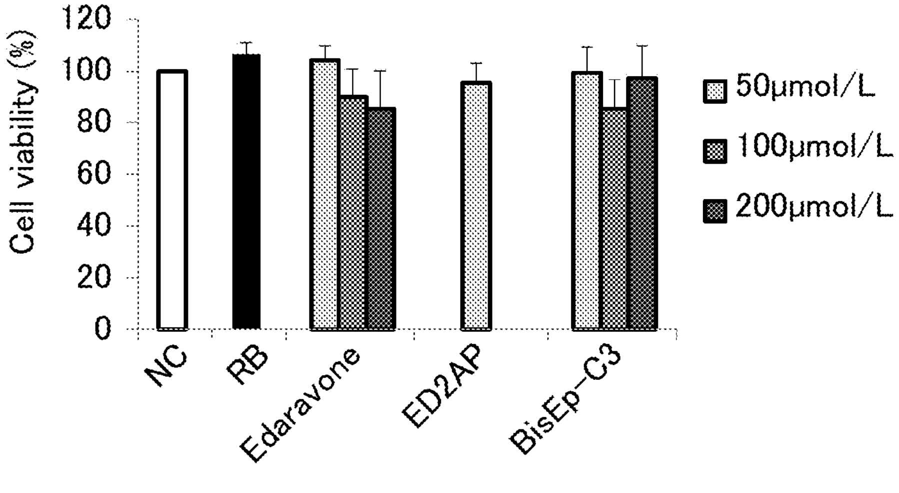
FIG. 6 is a graph showing the cell viability in Example 7.

FIG. 6 is a graph showing the cell viability. In FIG. 6, the horizontal axis indicates the type of the compound or the concentration of the compound and the vertical axis indicates the cell viability. As shown in FIG. 6, the byproducts of edaravone, ED2AP, and BisEp-C3 were not cytotoxic at any concentration.

These results showed that the vasodilator of the present invention has low cytotoxicity and that the byproduct obtained after reacting the vasodilator of the present invention with singlet oxygen has low cytotoxicity.

Example 8

It was examined that the compound included in the vasodilator of the present invention forms a conjugated system and has a tautomer.

(1) ED2AP

ED2AP was dissolved in $CDCl_3$ or DMSO, and a $^1$H-NMR spectrum was acquired using an NMR device (AV-600, Bruker). When $CDCl_3$ was used as a solvent, the frequency was 600 MHz, the compound concentration was 20 mg/ml, the temperature was 333 K, and the internal standard was tetramethylsilane. When DMSO was used as a solvent, the measurement conditions were the same as those in the case of using $CDCl_3$ as a solvent except that the temperature was 298 K. The results are shown in FIG. 7.

Figure 7A:
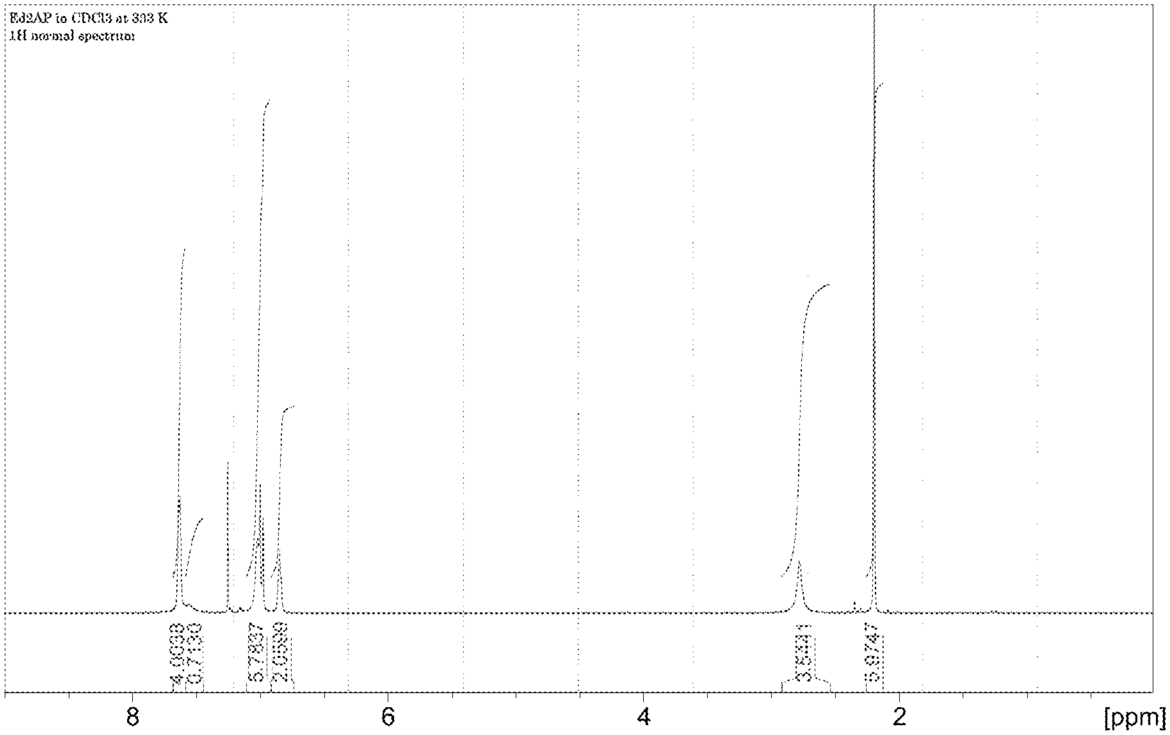
FIG. 7 shows graphs showing the $^{1}$H-NMR spectrum in Example 8.
Figure 7B:
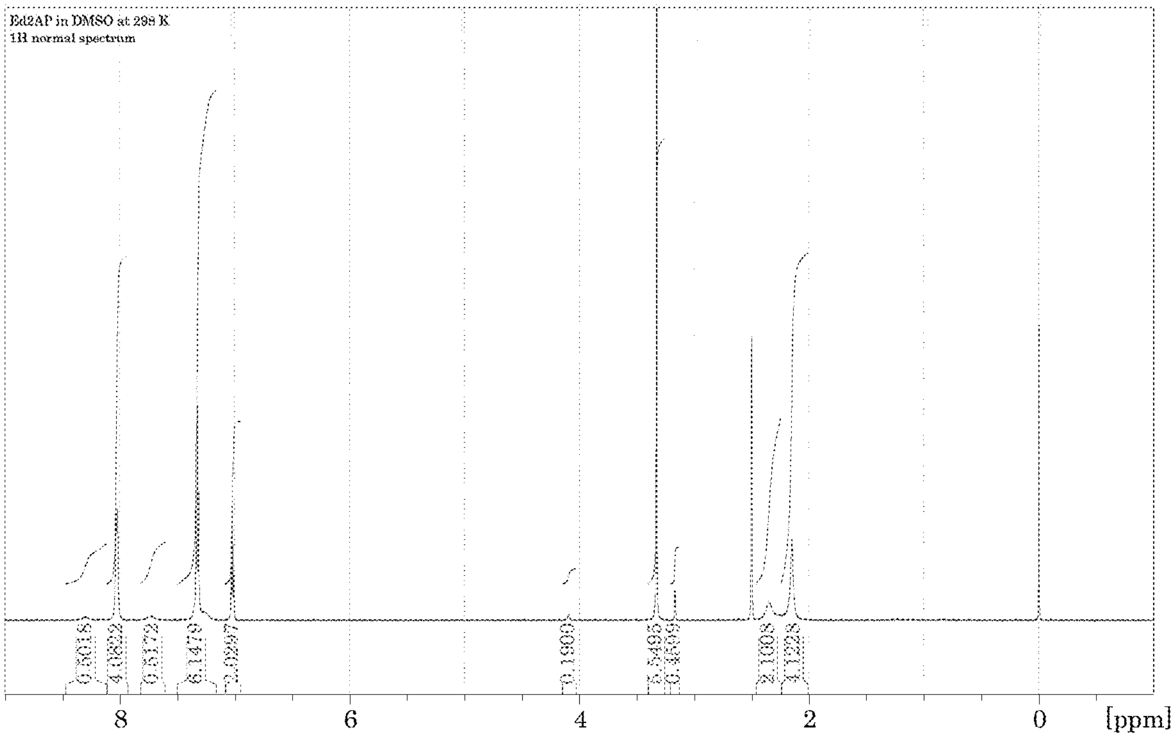

FIG. 7 shows graphs displaying an NMR spectrum. In FIG. 7, (A) shows the result when $CDCl_3$ was used and (B) shows the result when DMSO was used. In FIG. 7, the horizontal axis indicates the chemical shift value, and the vertical axis indicates the relative intensity. As shown in FIG. 7, three signals (8.02, 7.33, and 7.03) of the benzene ring and signals of three protons bonded to the conjugated double bond of the crosslinking part have been observed to be broad by chemical exchange by keto-enol rearrangement, and it was found that the linker region (L) forms a conjugated system. Also, of the three protons, one proton in the center was observed in two portions at 8.30 ppm and 7.74 ppm at the lowest magnetic field, and two protons close to edaravone at both ends were observed at 7.32 ppm and 7.26 ppm, and the effect also appears on the methyl group, resulting in two signals (2.35 ppm and 2.15 ppm). These showed that an isomer of cis-cis, cis-trans, trans-cis, or trans-trans was formed by the two double bonds of L. From these, it was found that, since the keto-enol isomerism occurs and the position of the double bond moves between neighboring atoms in the hydroxy group of $R^3$, ED2AP forms a tautomer of the following formula D and a geometric isomer (cis-trans isomer) of a geometric isomer (cis-trans isomer) of a tautomer of the following formula D.

[formula D]

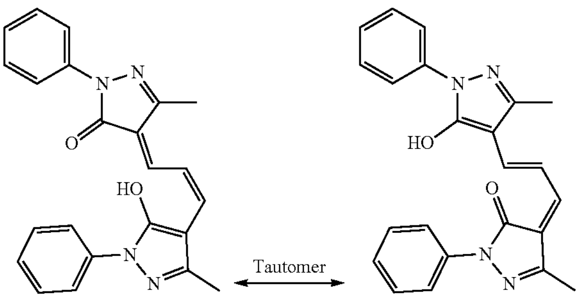

(2) BisEp-C3

BisEp-C3 (Bis-MP-C3) was dissolved in $CDCl_3$, and the $^1$H-NMR spectrum and the $^{13}$C-NMR spectrum were acquired using the NMR device. In acquiring the $^1$H-NMR spectrum, the frequency was 600 MHz, the compound concentration was 20 mg/ml, the temperature was 298 K or 313 K, and the internal standard was tetramethylsilane. In acquiring the $^{13}$C-NMR spectrum, the measurement conditions were the same as those in the case of acquiring the $^1$H-NMR spectrum except that the temperature was 298 K and the frequency was 150 MHz. The chemical shift value and the J coupling value were also calculated based on the $^1$H-NMR spectrum and the $^{13}$C-NMR spectrum. The results are shown in FIGS. 8 and 9 and Table 2.

TABLE 2

| | | 1H (ppm) | Integral value | J | 13C (ppm) |
|---|---|---|---|---|---|
| 2-ethyl group | CH3 | 1.29 | 6 | t 7.2 Hz | 14.1 |
| 2-ethyl group | CH2 | 3.85 | 4 | q 7.2 Hz | 39.7 |
| 3-one | C═O | | | | 161.6 |
| | C4 | | | | 111.5 |
| | C5 | | | | 147.4 |
| 5-methyl | CH3 | 2.31 | 6 | | 14.3 |
| Both ends of cross-linking part (L) | CH | 7.40 | 2 | d 13.4 Hz | 146.3 |
| Center of cross-linking part (L) | CH | 7.74 | 1 | t 13.4 Hz | 117.4 |
| | OH | 9.21 | 1.4 | | |

Figure 8A:
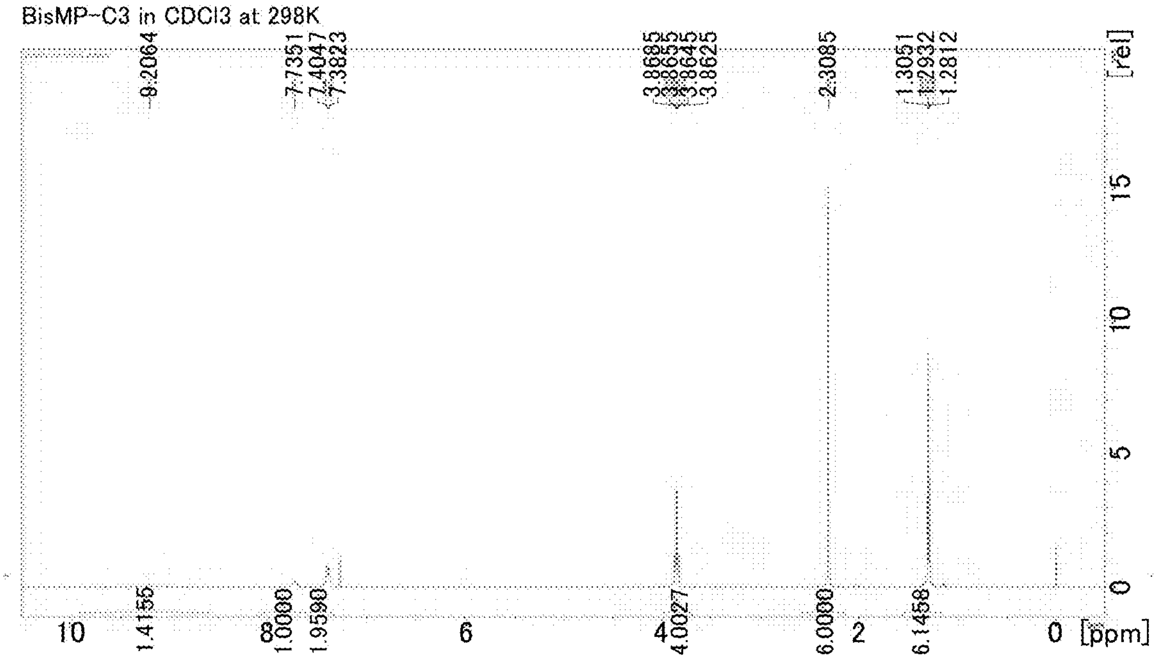
FIG. 8 shows graphs showing the $^{1}$H-NMR spectrum in Example 8.
Figure 8B:
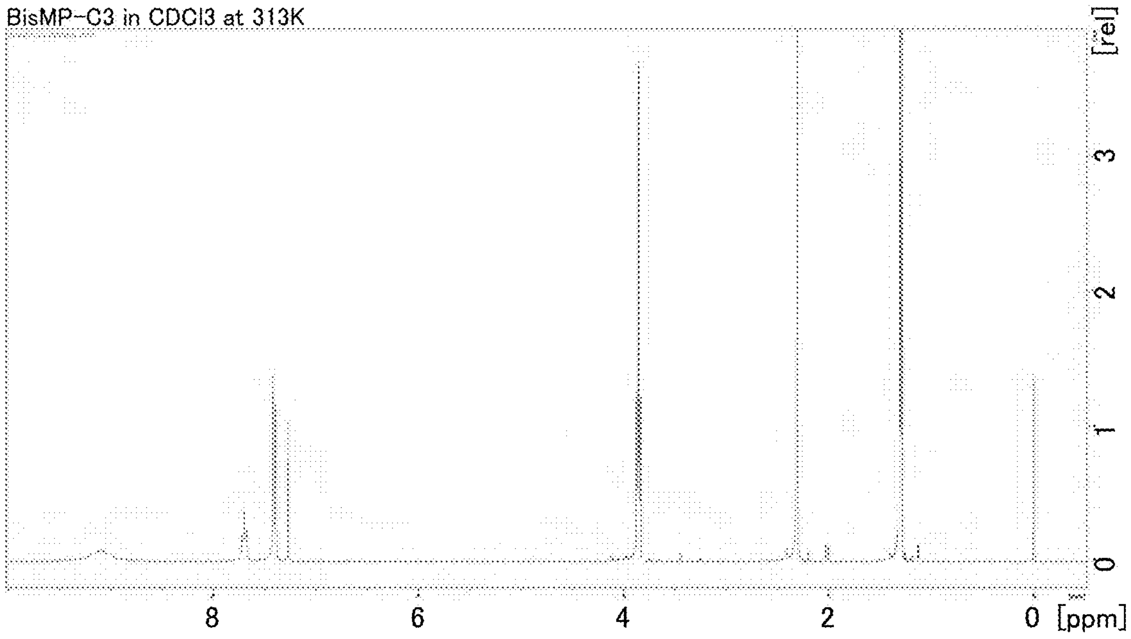
Figure 9:
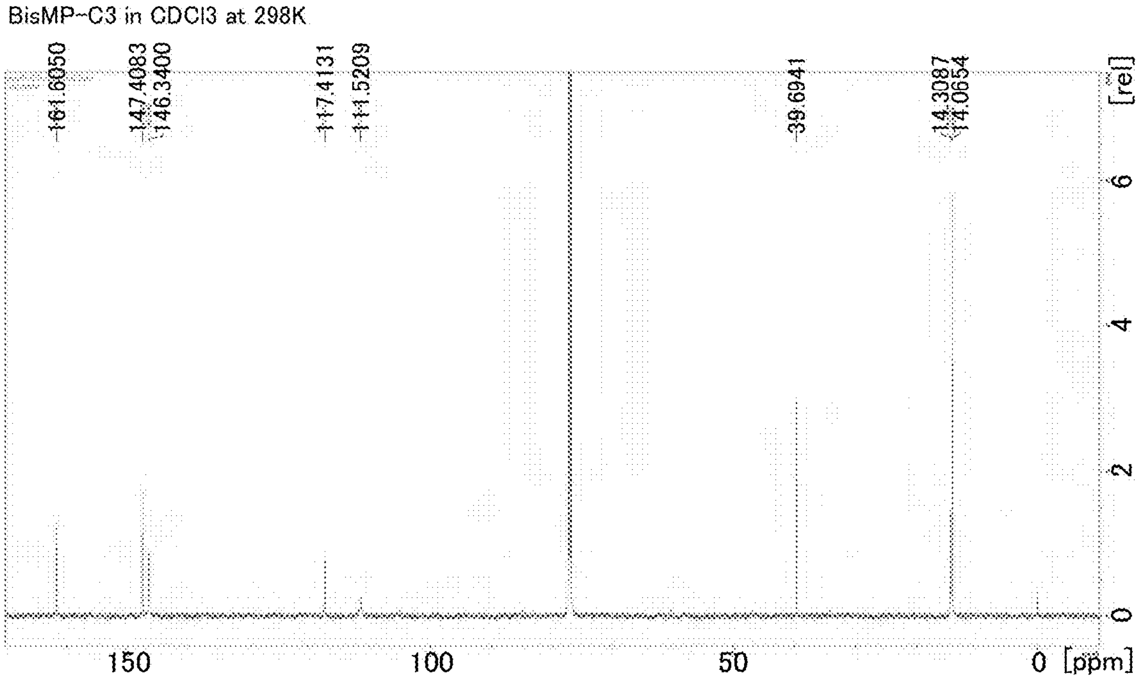
FIG. 9 is a graph showing the $^{13}$C-NMR spectrum in Example 8.

FIG. 8 shows graphs displaying the $^1$H-NMR spectrum and FIG. 9 is a graph showing the $^{13}$C-NMR spectrum. In FIG. 8, (A) shows the result of 298 K, and (B) shows the result of 313 K. In FIGS. 8 and 9, the horizontal axis indicates the chemical shift value and the vertical axis indicates the relative intensity. As shown in FIG. 8, three signals (7.73, 7.40, and 7.38) of the benzene ring and signals of three protons bonded to the conjugated double bond of the crosslinking part have been observed to be broad by chemical exchange by keto-enol rearrangement, and it was found that the linker region (L) forms a conjugated system. Also, of the three protons, one proton in the center was observed at 7.74 ppm at the lowest magnetic field, and two protons close to edaravone at both ends were observed at 7.40 ppm, and the effect also appears on the methyl group, resulting in a signal (2.31 ppm). These showed that an isomer of cis-cis, cis-trans, trans-cis, or trans-trans was formed by the two double bonds of L. These results showed that, since the keto-enol isomerism occurs and the position of the double bond moves between neighboring atoms in the hydroxy group of $R^3$, BisEp-C3 forms a tautomer of the following formula E and a geometric isomer (cis-trans isomer) of a geometric isomer (cis-trans isomer) of a tautomer of the following formula E.

[formula E]

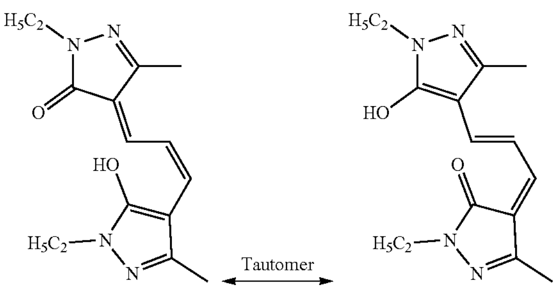

These results showed that the compound contained in the vasodilator of the present invention forms a conjugated system and has a tautomer. The results also suggested that a similar conjugated system establishes when L is an alkenyl group having an even number of carbon atoms.

Example 9

It was examined that the vasodilator of the present invention dilates blood vessels in vivo.

Oxidative stress caused by ROS is known to reduce NO production in vascular endothelial cells, resulting in vasoconstriction and decreased blood flow. Therefore, using vasodilation as an indicator, it was examined whether the vasodilator of the present invention scavenges RSO in vivo.

Eight-week-old or older female rats (Wistar, body weight: approximately 200 g, n=1) were anesthetized by subcutaneous administration of urethane so as to be 7 g/kg body weight. The hair of the auricles of the rats was then removed and the rats were fixed on a fixing table. After the fixing, the fixing table was placed under a microscope (Nikon OPTIphoto, produced by Nikon Corporation). In addition, a catheter was placed in the groin vein of the rat.

BisEP-C3 was dissolved in a saline solution to achieve a concentration of 3 mg/ml. The resulting saline solution containing BisEP-C3 was administered intravenously via the catheter so as to be 3 mg/kg body weight. Then, the hemodynamic course of the rat auricular subcutaneous blood vessel was photographed and recorded using a microscope at a predetermined period (30, 60, 120 or 180 minutes) before and after the administration.

The obtained images were classified into three blood vessel thicknesses (thick: 35-45 μm, medium: 15-20 μm, thin: 7-9 μm) based on the diameter of the blood vessel before administration. Next, in the vein in the obtained image, a plurality of sites where there was no branch of the blood vessel and the blood vessel was in focus were selected for each classification of the blood vessel. Further, for each selected site, the relative blood vessel diameter was calculated after the measurement of the blood vessel diameter, with the blood vessel diameter before administration being a reference (1). Then, the average value of the relative blood vessel diameters was obtained for each classification of the blood vessel diameters. As a control, the blood vessel diameter was calculated in the same manner except that the saline solution was administered. The results are shown in FIG. 10.

Figure 10A:
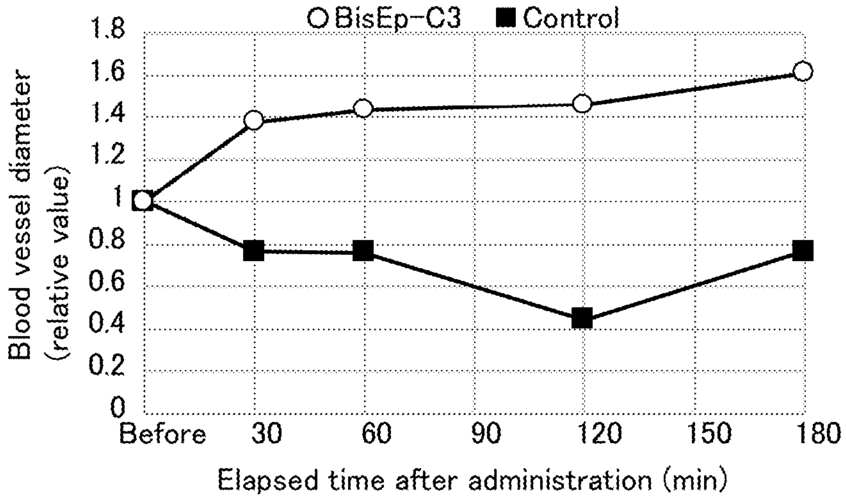
FIG. 10 shows graphs showing change of the blood vessel diameter after administration of the vasodilator of the present invention in Example 9.
Figure 10B:
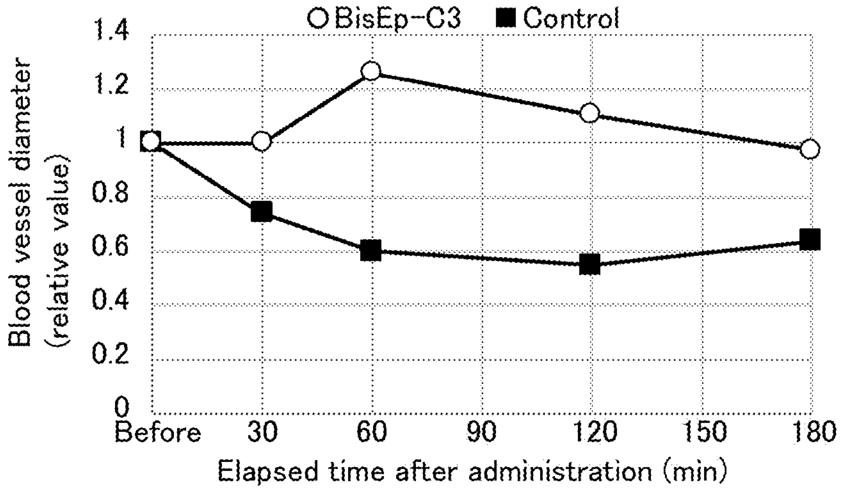
Figure 10C:
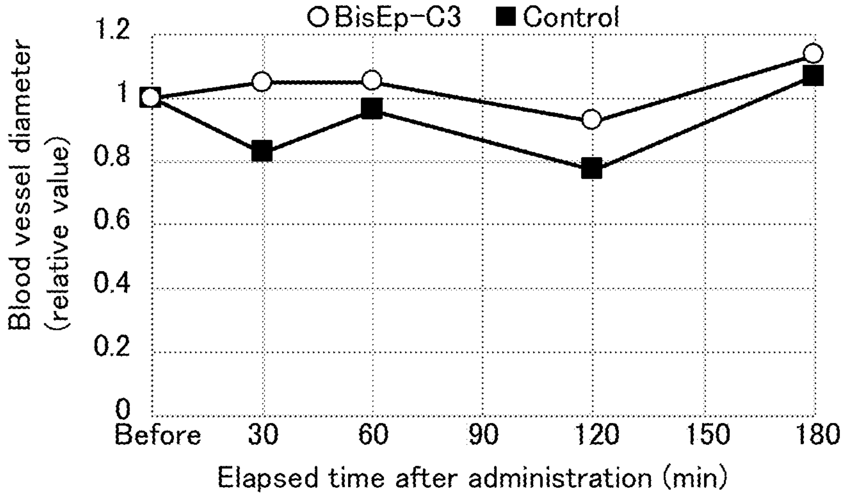
Figure 11A:
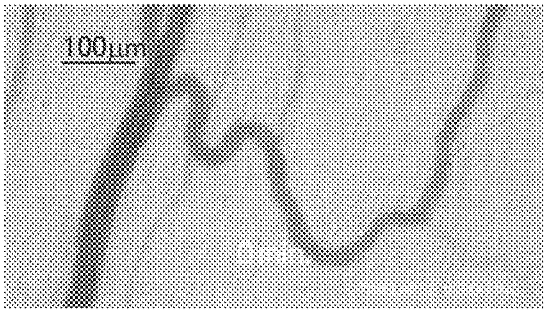
FIG. 11 shows photographs showing the results of the mesentery of the control in Example 10.
Figure 11B:
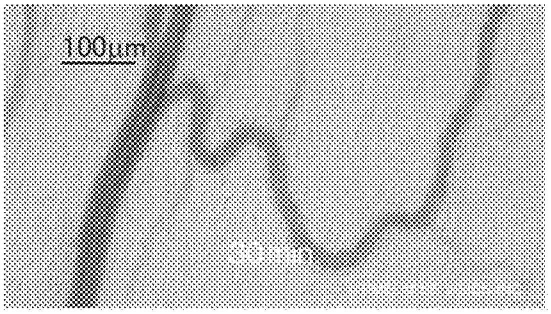
Figure 11C:
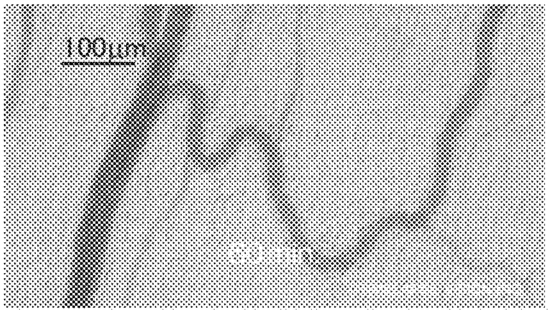
Figure 11D:
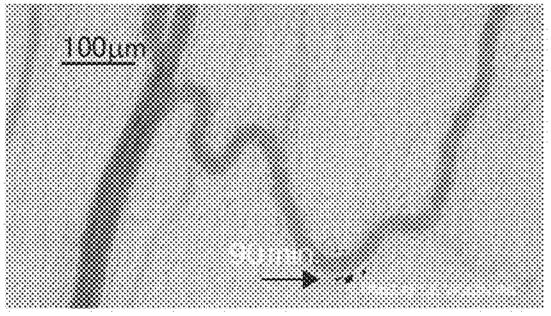
Figure 11E:
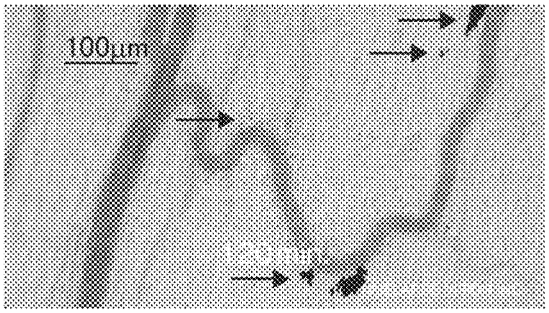
Figure 11F:
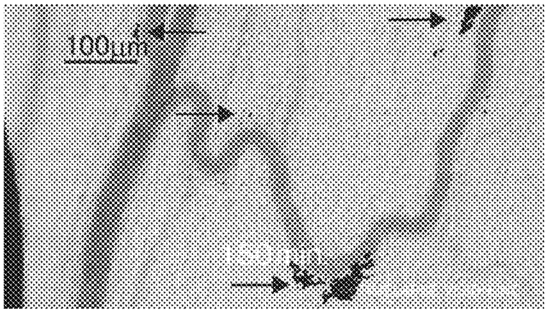
Figure 11G:
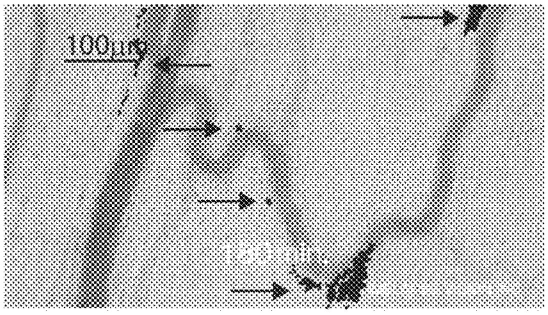
Figure 12A:
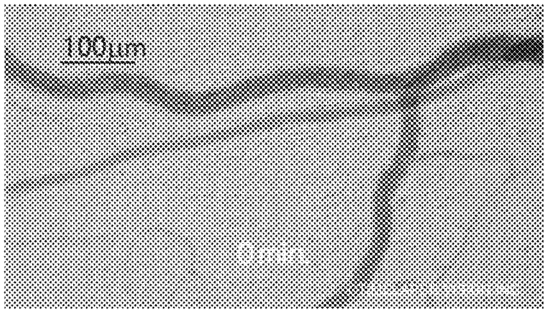
FIG. 12 shows photographs showing the results of the mesentery of rats administered with BisEP-C3 in Example 10.
Figure 12B:
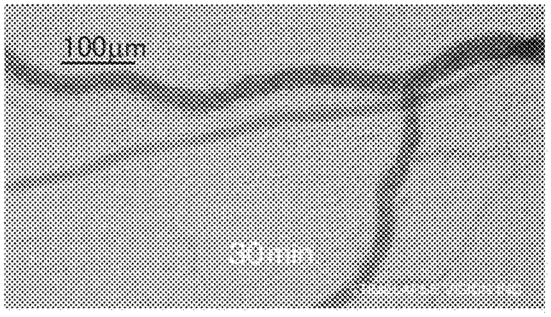
Figure 12C:
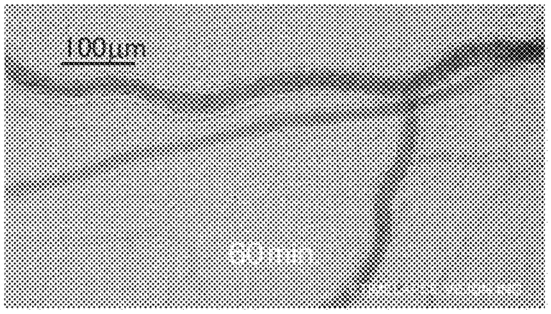
Figure 12D:
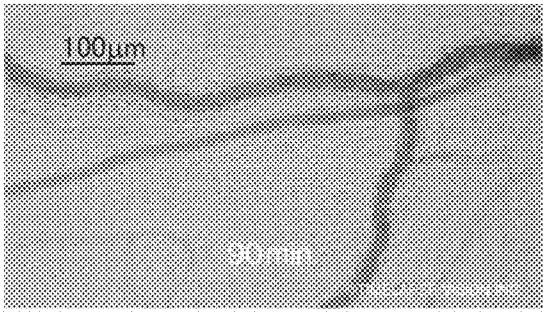
Figure 12E:
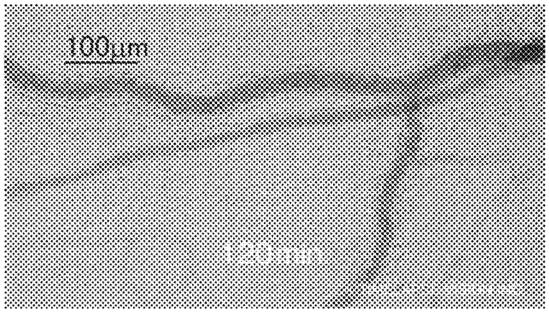
Figure 12F:
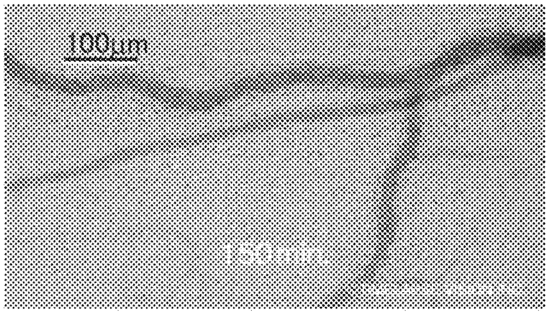
Figure 12G:
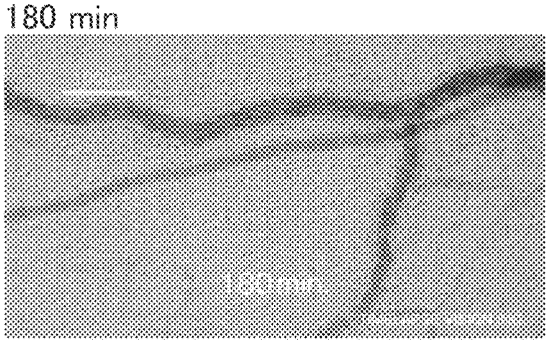

FIG. 10 shows graphs displaying the change of blood vessel diameter after administration of the vasodilator of the present invention. In FIG. 10, (A) shows the result of a thin blood vessel, (B) shows the result of a medium blood vessel, and (C) shows the result of a thick blood vessel. In FIG. 10A to 10C, the horizontal axis indicates the elapsed time after administration and the vertical axis indicates the relative value of the blood vessel diameter. As shown in FIG. 10A to 10C, when BisEp-C3 was administered, the blood vessel diameter was dilated at any time after administration as compared to the control. Further, while the blood vessel diameter was dilated regardless of the size of the blood vessel when BisEp-C3 was administered, the severity of dilatation of the blood vessel diameter was remarkably observed in the smaller blood vessels. These results showed that the vasodilator of the present invention can induce vasodilation in vivo. Also, as described above, oxidative stress caused by ROS reduces NO production in vascular endothelial cells, resulting in vasoconstriction and decreased blood flow. Since the vasodilator of the present invention can eliminate ROS and induce vasodilation in vivo, it was found that the vasodilator of the present invention eliminates ROS and reduces oxidative stress, thereby enhancing NO production in vascular endothelial cells, resulting in vasodilation.

Example 10

It was examined that the protective agent of the present invention prevents vascular disorder in vivo.

Eight-week-old or older female rats (Wistar, body weight: approximately 200 g, n=1) were anesthetized by subcutaneous administration of urethane (1.75 g/kg body weight). The rats were then opened and fixed on a fixing table in such a manner that the mesentery of the rats was observable. After the fixing, the fixing table was placed under a microscope (Nikon OPTIphoto, produced by Nikon Corporation) so that the mesentery could be observed. In addition, a catheter was placed in the groin vein of the rat.

1μg/ml of lipopolysaccharide (LPS) (produced by Sigma-Aldrich Co., Ltd.) derived from Pseudomonas aeruginosa (ATCC27316) was added dropwise once (20 μl, 20 ng/sight) and allowed to stand for 30 minutes. Next, a saline solution containing BisEP-C3 prepared in the same manner as in Example 9 was rapidly administered intravenously via the catheter so as to be 1 mg/kg body weight. After the intravenous administration, the saline solution was administered continuously so as to be 1 mg/kg body weight per hour (0.15 ml/hour). In addition, in parallel with the administration of the saline solution containing LPS and BisEP-C3, one visual field, including the blood vessel of the mesentery, was photographed over time. In the obtained photograph, the area of the region where bleeding occurred (bleeding area) was detected based on the number of pixels, and then the proportion of the area (bleeding area proportion) occupied per visual field was calculated. As a control, the experiment was performed in the same manner except that a saline solution was administered instead of the saline solution containing BisEP-C3. The results are shown in FIGS. 11 to 13.

FIG. 11 shows photographs displaying the results of the mesentery of the control, and (A) to (G) are photographs at the time of LPS instillation (0 minutes) and 30, 60, 90, 120, 150, and 180 minutes after LPS instillation, respectively. In FIG. 11, a black region indicated by an arrow is a region in which bleeding has occurred.

FIG. 12 shows photographs displaying the results of the mesentery of rats administered with BisEP-C3, and (A) to (G) are photographs at the time of LPS instillation (0 minutes) and at 30, 60, 90, 120, 150, and 180 minutes after LPS instillation, respectively.

Figure 13A:
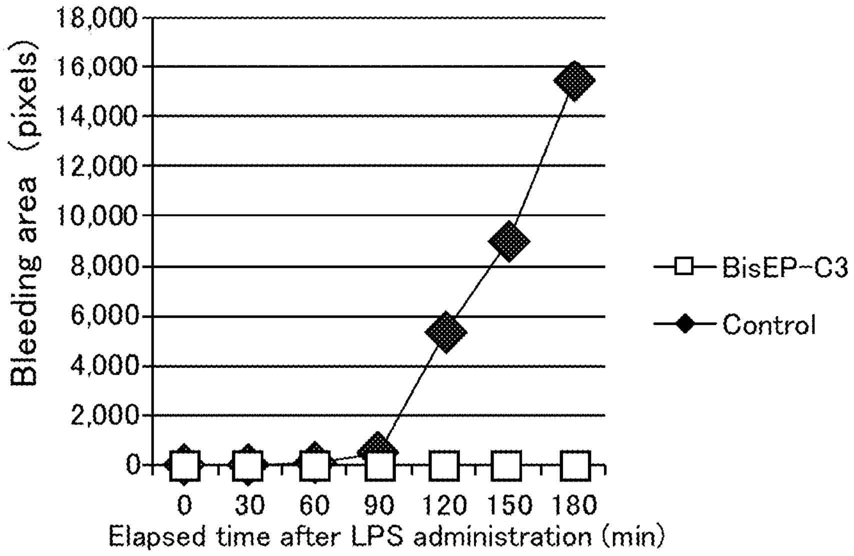
FIG. 13 shows graphs showing the bleeding area and the bleeding area proportion in Example 10.
Figure 13B:
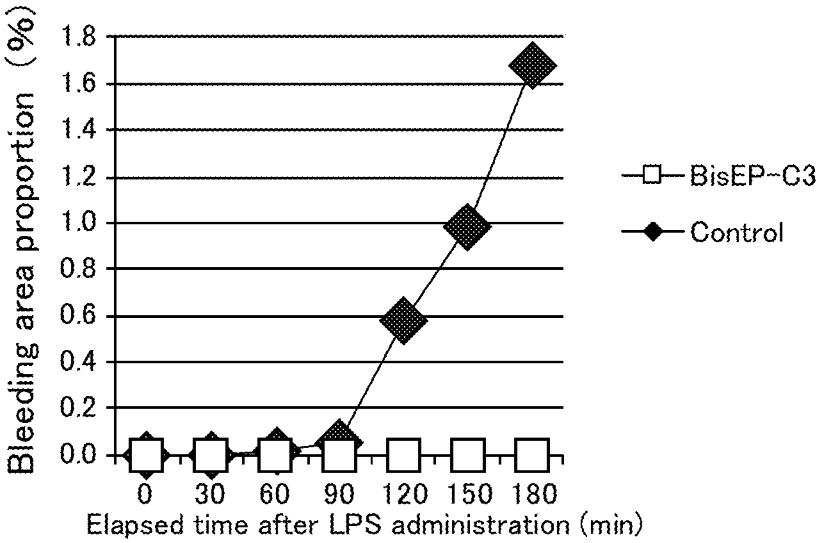

FIG. 13 shows graphs displaying the bleeding area and the bleeding area proportion. In FIG. 13, (A) shows the result of the bleeding area, and (B) shows the result of the bleeding area proportion. In (A) in FIG. 13, the horizontal axis indicates elapsed time after LPS administration, and the vertical axis indicates the bleeding area. In (B) in FIG. 13, the horizontal axis indicates elapsed time after LPS administration, and the vertical axis indicates the bleeding area proportion. As shown in FIGS. 11 and 13, in the control, bleeding to the periphery was observed in the mesenteric blood vessel from 90 minutes after LPS administration, and the region of bleeding increased with time. In contrast, as shown in FIGS. 12 and 13, in the BisEP-C3 administration group no bleeding was observed after the LPS administration. Administration of LPS generates ROS in the organism and causes vascular disorders. Therefore, it was presumed that the protective agent of the present invention prevents vascular disorders by scavenging the ROS in vivo.

In addition, the rolling phenomena of leukocytes in the blood of rats administered with BisEP-C3 and controls were examined over time after LPS instillation. In the control, no rolling phenomenon of leukocytes was observed in the blood vessel after LPS instillation. This is thought to be because the instillation of LPS increases the NO production by inducible NO synthase and also increases the production of ROS from neutrophils, so that NO reacts with superoxide in ROS to form peroxynitrite with high oxidizing power, exhibits cytotoxicity, and causes vascular disorders. In contrast, a large number of rolling phenomena of leukocytes were observed in rats administered with BisEP-C3 as compared to the control. This is thought to be because, although the instillation of LPS increases the NO production by inducible NO synthase and also increases the production of ROS from neutrophils, BisEP-C3 scavenges ROS and reduces the peroxynitrite production, thereby suppressing the cytotoxicity.

These results showed that the protective agent of the present invention prevents vascular disorder in vivo.

Example 11

It was examined that the vasodilator of the present invention has NO-eliminating ability.

Figure 14:
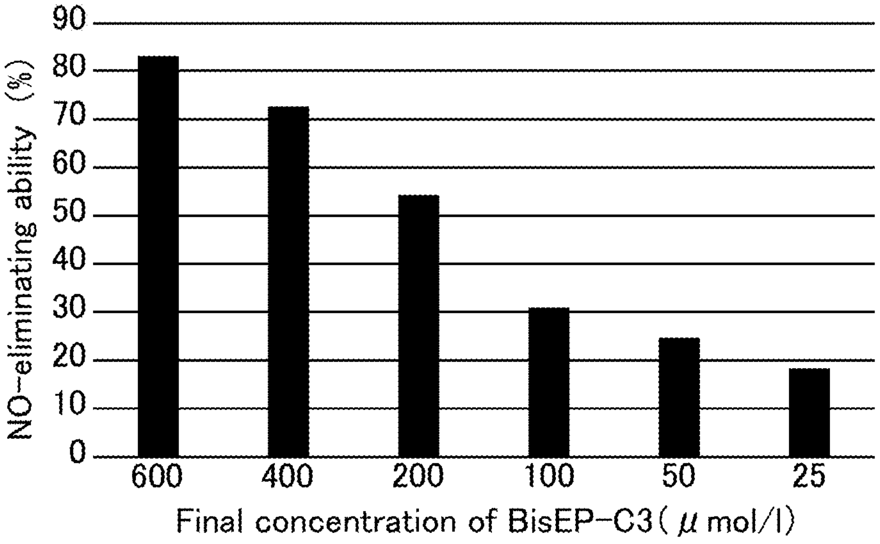
FIG. 14 is a graph showing the suppression ratio of NO in Example 11.

It was examined whether the vasodilator of the present invention has NO-eliminating ability. Specifically, as to the NO generation reaction, NOC-7 of NO donor was used to examine whether the NO concentration is reduced in the presence of BisEP-C3. First, 20 μl of a BisEp-C3 solution was added to 140 μl of a phosphate buffer solution (pH 7.4) having a concentration of 0.1 μmol/1 so as to achieve a predetermined concentration (0, 25, 50, 100, 200, 400, or 600 μmol/1), and further 20 μl of a spin-trapping agent (100 μmol/1), Carboxy-PTIO(2-(4-Carboxyphenyl)-4, 4, 5, 5-tetramethylimidazoline-1-oxyl-3-oxide, sodium salt, final concentration 10 μmol/1) solution and 20 μl of a NO donor solution (10 mmol/1NOC-7 (1-Hydroxy-2-oxo-3-(N-methyl-3-aminopropyl)-3-methyl-1-triazene, final concentration 1.0 μmol/1)) were added and mixed. The NO donor solution was prepared using a sodium hydroxide solution having a concentration of 0.1 mmol/1. Then, after the mixing, the mixture was incubated at room temperature for 3 minutes, and the obtained reaction solution was measured under the following ESR measurement conditions 2. Then, the proportion of the decrease in the signal intensity was calculated as the NO-eliminating ability with the signal intensity of the sample with no BisEP-C3 (0 μmol/1) being 100%. These results are shown in FIG. 14.

ESR Measurement Conditions 2

Equipment:

Electron spin resonance spectrometer (JES-TE-300, produced by Japan Electron Optics Laboratory Co. Ltd.)

Measurement conditions:

Microwave output: 8 mW

Sweep time: 1 minute

Sweep width: 335.5±5 mT

Magnetic field modulation: 100 kHz 0.079 mT

Gain: ×32

Time constant: 0.03 sec

FIG. 14 is a graph showing the NO-eliminating ability. In FIG. 14, the horizontal axis indicates the final concentration of BisEP-C3 and the vertical axis indicates the NO-eliminating ability. As shown in FIG. 14, BisEP-C3 eliminated NO in a concentration-dependent manner. These results showed that the vasodilator of the present invention has the NO-eliminating ability. Note that, when comparing the NO-eliminating ability with the relative value of the production amount of superoxide in Example 3 in BisEP-C3 having an equal concentration, the proportion of the decrease in the production amount of superoxide is larger than the NO-eliminating ability. Thus, it was presumed that the vasodilator of the present invention has a higher-eliminating ability for superoxide compared with that for NO.

As described above, NO is believed to react with ROS to form highly oxidative peroxynitrite ($ONOO^-$), causing vascular disorder. It was presumed that the vasodilator of the present invention suppresses the production of peroxynitrite and suppresses vascular disorder by having a NO-eliminating ability in addition to a ROS-eliminating ability involved in the production of peroxynitrite. In addition, the vasodilator of the present invention also has an eliminating ability against NO having a vasodilation action. However, the NO-eliminating ability is relatively lower than the ROS-eliminating ability. Therefore, it was presumed that the reason why vasodilation occurs when the vasodilator of the present invention is administered in vivo is that the vasodilator of the present invention preferentially reacts with ROS to eliminate.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2019-228695 filed on Dec. 18, 2019. The entire subject matter of the Japanese Patent Application is incorporated herein by reference.

(Supplementary Notes)

Some or all of the above embodiments and examples may be described as in the following Supplementary Notes, but are not limited thereto.

(Supplementary Note 1)

A vasodilator including:

a compound represented by the following formula (1) or a salt thereof:

(1)

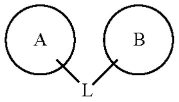

where in the formula (1), an A ring and a B ring may be the same or different and are each a pyrazole ring having a substituent or a pyrazoline ring having a substituent, and L is a saturated or unsaturated hydrocarbon group.

(Supplementary Note 2)

The vasodilator according to Supplementary Note 1, wherein:

the A ring and the B ring may be the same or different and are represented by the following formula (2) or (3):

(2)

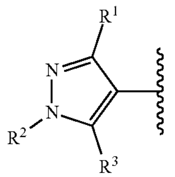

(3)

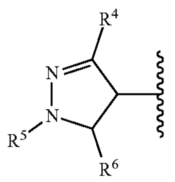

where in the formula (2), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent; and where in the formula (3), $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent.

(Supplementary Note 3)

The vasodilator according to Supplementary Note 1 or 2, wherein,

L is an unsaturated hydrocarbon group having 1 to 6 carbon atoms.

(Supplementary Note 4)

The vasodilator according to any one of Supplementary Notes 1 to 3, wherein:

the compound represented by the formula (1) includes a compound represented by the following formula (4):

(4)

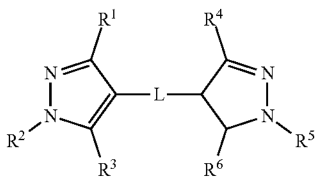

where in the formula (4), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^4$ is a hydrogen atom, a halogen atom, or an alkyl group, $R^5$ is an alkyl group or an aryl group that may have a substituent, $R^6$ is a hydrogen atom, an oxygen atom, a halogen atom, or a hydroxy group, and L is a saturated or unsaturated hydrocarbon group having 1 to 6 carbon atoms.

(Supplementary Note 5)

The vasodilator according to any one of Supplementary Notes 1 to 4, wherein:

the compound represented by the formula (1) includes a compound represented by the following formula (5):

(5)

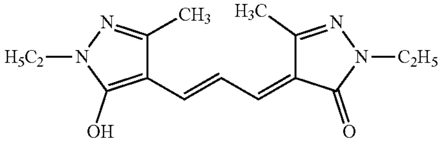

(Supplementary Note 6)

The vasodilator according to any one of Supplementary Notes 1 to 4, wherein:

the compound represented by the formula (1) includes a compound represented by the following formula (6):

(6)

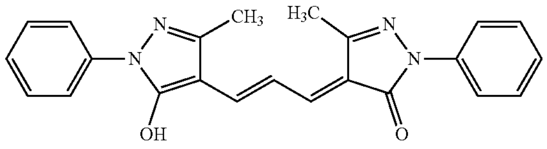

(Supplementary Note 7)

The vasodilator according to any one of Supplementary Notes 1 to 3, wherein:

the compound represented by the formula (1) includes a compound represented by the following formula (12):

(12)

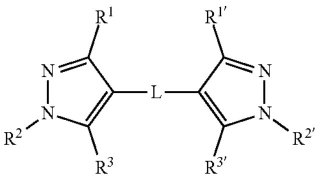

where in the formula (12), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^{1'}$ is a hydrogen atom, a halogen atom, or an alkyl group, $R^{2'}$ is an alkyl group or an aryl group that may have a substituent, $R^{3'}$ is a hydrogen atom, a halogen atom, an alkyl group, or a hydroxy group, and L is a saturated or unsaturated hydrocarbon group having 1 to 6 carbon atoms.

(Supplementary Note 8)

The vasodilator according to any one of Supplementary Notes 1, 2, and 7, wherein:

the compound represented by the formula (1) includes a compound represented by the following formula (13):

(13)

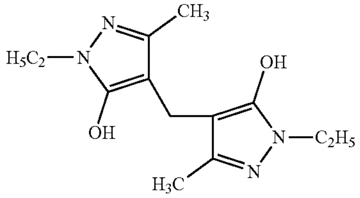

(Supplementary Note 9)

A bloodstream-improving agent including:

the vasodilator according to any one of Supplementary Notes 1 to 8.

(Supplementary Note 10)

A vascular disorder protective agent, including:

the vasodilator according to any one of Supplementary Notes 1 to 8.

(Supplementary Note 11)

A pharmaceutical for a disease caused by vascular stenosis, including:

the vasodilator according to any one of Supplementary Notes 1 to 8.

(Supplementary Note 12)

The pharmaceutical according to Supplementary Note 11, wherein:

the disease caused by vascular stenosis is cardiovascular disease, respiratory system disease, central nervous system disease, digestive system disease, hematological disease, endocrine system disease, urological disease, skin disease, supporting tissue disease, eye disease, tumor, iatrogenic disease, environmental contamination-induced disease, or dental disease.

(Supplementary Note 13)

A vasodilation method using the vasodilator according to any one of Supplementary Notes 1 to 8.

(Supplementary Note 14)

The vasodilation method according to Supplementary Note 13, including the step of:

contacting with the vasodilator.

(Supplementary Note 15)

The vasodilation method according to Supplementary Note 14, wherein:

the vasodilator is contacted in vitro or in vivo.

(Supplementary Note 16)

A method for treating a disease caused by vascular stenosis, including the step of:

administering to a patient the pharmaceutical according to Supplementary Note 11 or 12.

(Supplementary Note 17)

The method according to Supplementary Note 16, wherein:

the disease caused by vascular stenosis is a cardiovascular disease, respiratory system disease, central nervous system disease, digestive system disease, hematological disease, endocrine system disease, urological disease, skin disease, supporting tissue disease, eye disease, tumor, iatrogenic disease, environmental contamination-induced disease, or dental disease.

(Supplementary Note 18)

Use of a compound represented by the following formula (1) or a salt thereof for use in vasodilation:

(1)

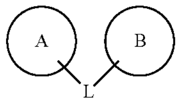

where in the formula (1), an A ring and a B ring may be the same or different and are each a pyrazole ring having a substituent or a pyrazoline ring having a substituent, and L is a saturated or unsaturated hydrocarbon group.

(Supplementary Note 19)

Use of a compound represented by the following formula (1) or a salt thereof for use in bloodstream improvement:

(1)

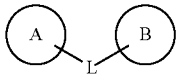

where in the formula (1), an A ring and a B ring may be the same or different and are each a pyrazole ring having a substituent or a pyrazoline ring having a substituent, and L is a saturated or unsaturated hydrocarbon group.

(Supplementary Note 20)

Use of a compound represented by the following formula (1) or a salt thereof for use in treatment of a disease caused by vascular stenosis:

(1)

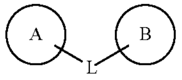

where in the formula (1), an A ring and a B ring may be the same or different and are each a pyrazole ring having a substituent or a pyrazoline ring having a substituent, and L is a saturated or unsaturated hydrocarbon group.

Industrial Applicability

As described above, according to the present invention, by including the compound represented by the formula (1) or a salt thereof, blood vessels can be dilated. Thus, the vasodilator of the present invention can be used, for example, as a protective agent against the cellular dysfunction caused by the vascular stenosis, and can be used, for example, as a pharmaceutical for a disease caused by vascular stenosis. Therefore, the present invention is extremely useful, for example, in the field of pharmaceuticals and the like.

The invention claimed is:

1. A vasodilation method using a vasodilator, wherein the vasodilator comprises:

a compound represented by the following formula (1) or a salt thereof:

(1)

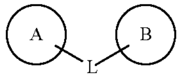

where in the formula (1), an A ring and a B ring may be the same or different and are each a pyrazole ring having a substituent or a pyrazoline ring having a substituent, and L is a saturated or unsaturated hydrocarbon group, the method comprising administering the vasodilator to a patient with a disease caused by vascular stenosis, and the disease caused by vascular stenosis is hematological disease, cardiovascular disease, central nervous system disease, digestive system disease, respiratory system disease, urological disease, or dental disease.

2. The vasodilation method according to claim 1, the method comprising:

contacting with the vasodilator in vitro or in vivo.

3. The vasodilation method according to claim 1, wherein the A ring and the B ring may be the same or different and are represented by the following formula (2) or (3):

(2)

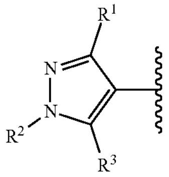

(3)

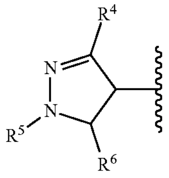

where in the formula (2), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and where in the formula (3), $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent.

4. The vasodilation method according to claim 1, wherein

L is an unsaturated hydrocarbon group having 1 to 6 carbon atoms.

5. The vasodilation method according to claim 1, wherein the compound represented by the formula (1) comprises a compound represented by the following formula (4):

(4)

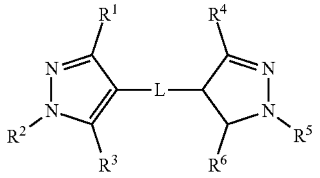

where in the formula (4), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^4$ is a hydrogen atom, a halogen atom, or an alkyl group, $R^5$ is an alkyl group or an aryl group that may have a substituent, $R^6$ is a hydrogen atom, an oxygen atom, a halogen atom, or a hydroxy group, and L is a saturated or unsaturated hydrocarbon group having 1 to 6 carbon atoms.

6. The vasodilation method according to claim 1, wherein the compound represented by the formula (1) comprises a compound represented by the following formula (5):

(5)

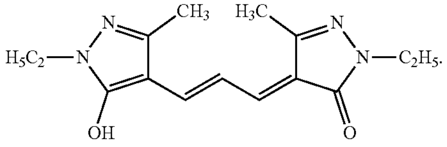

7. The vasodilation method according to claim 1, wherein the compound represented by the formula (1) comprises a compound represented by the following formula (6):

(6)

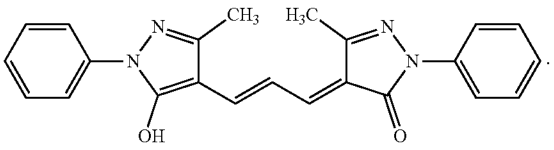

8. The vasodilation method according to claim 1, wherein the compound represented by the formula (1) comprises a compound represented by the following formula (12):

(12)

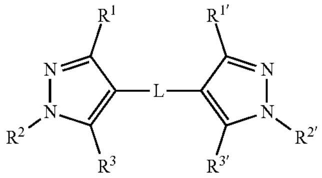

where in the formula (12), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^{1'}$ is a hydrogen atom, a halogen atom, or an alkyl group, $R^{2'}$ is an alkyl group or an aryl group that may have a substituent, $R^{3'}$ is a hydrogen atom, a halogen atom, an alkyl group, or a hydroxy group, and L is a saturated or unsaturated hydrocarbon group having 1 to 6 carbon atoms.

9. The vasodilation method according to claim 1, wherein the compound represented by the formula (1) comprises a compound represented by the following formula (13):

(13)

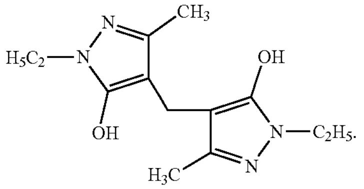

10. A method for treating a disease caused by vascular stenosis, the method comprising:

administering to a patient a compound represented by the following formula (1) or a salt thereof:

(1)

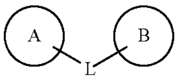

where in the formula (1), an A ring and a B ring may be the same or different and are each a pyrazole ring having a substituent or a pyrazoline ring having a substituent, and L is a saturated or unsaturated hydrocarbon group, and the disease caused by vascular stenosis is hematological disease, cardiovascular disease, central nervous system disease, digestive system disease, respiratory system disease, urological disease, or dental disease.

11. The method according to claim 10, wherein the A ring and the B ring may be the same or different and are represented by the following formula (2) or (3):

(2)

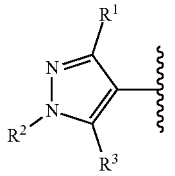

(3)

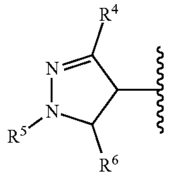

where in the formula (2), $R^1$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^2$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and $R^3$ is a hydrogen atom, a halogen atom, an alkyl group, an amino group, a cyano group, a hydroxy group, a sulfo group, a carboxyl group, an alkoxy group, a hydroxyalkyl group, an acyl group, an alkynyl group, or an aryl group that may have a substituent, and where in the formula (3), $R^4$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, $R^5$ is a hydrogen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent, and $R^6$ is a hydrogen atom, an oxygen atom, a halogen atom, an alkyl group, an amino group, a cyano group, a hydroxy group, a sulfo group, a carboxyl group, an alkoxy group, a hydroxyalkyl group, an acyl group, an alkenyl group, an alkynyl group, or an aryl group that may have a substituent.

12. The vasodilation method according to claim 1, wherein

L is an unsaturated hydrocarbon group having 1 to 6 carbon atoms.

13. The method according to claim 10, wherein the compound represented by the formula (1) comprises a compound represented by the following formula (4):

(4)

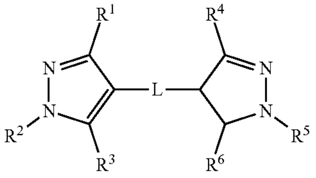

where in the formula (4), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^4$ is a hydrogen atom, a halogen atom, or an alkyl group, $R^5$ is an alkyl group or an aryl group that may have a substituent, $R^6$ is a hydrogen atom, an oxygen atom, a halogen atom, or a hydroxy group, and L is a saturated or unsaturated hydrocarbon group having 1 to 6 carbon atoms.

14. The method according to claim 10, wherein the compound represented by the formula (1) comprises a compound represented by the following formula (5):

(5)

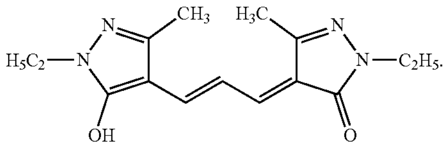

15. The method according to claim 10, wherein the compound represented by the formula (1) comprises a compound represented by the following formula (6):

(6)

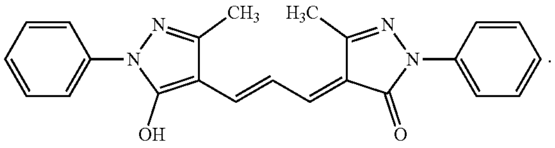

16. The method according to claim 10, wherein the compound represented by the formula (1) comprises a compound represented by the following formula (12):

(12)

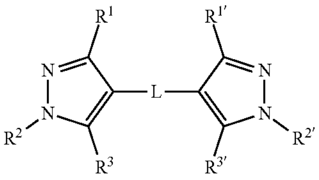

where in the formula (12), $R^1$ is a hydrogen atom, a halogen atom, or an alkyl group, $R^2$ is an alkyl group or an aryl group that may have a substituent, $R^3$ is a hydrogen atom, a halogen atom, or a hydroxy group, $R^{1'}$ is a hydrogen atom, a halogen atom, or an alkyl group, $R^{2'}$ is an alkyl group or an aryl group that may have a substituent, $R^{3'}$ is a hydrogen atom, a halogen atom, an alkyl group, or a hydroxy group, and L is a saturated or unsaturated hydrocarbon group having 1 to 6 carbon atoms.

17. The method according to claim 10, wherein the compound represented by the formula (1) comprises a compound represented by the following formula (13):

(13)

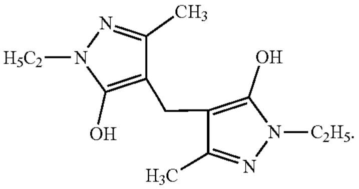

* * * * *